US008638435B2

(12) United States Patent
Strong et al.

(10) Patent No.: US 8,638,435 B2
(45) Date of Patent: Jan. 28, 2014

(54) MAGNETIC PARTICLE-BASED BIOASSAYS

(75) Inventors: Louis H. Strong, Duxbury, MA (US);
Clark M. Edson, Belmont, MA (US);
Senerath Palamakumbura, Winchester, MA (US); Daniel B. Hall, Easton, MA (US); Gyula Varadi, Watertown, MA (US)

(73) Assignee: Radiation Monitoring Devices, Inc., Watertown, MA (US)

( * ) Notice: Subject to any disclaimer, the term of this patent is extended or adjusted under 35 U.S.C. 154(b) by 58 days.

(21) Appl. No.: 13/191,813

(22) Filed: Jul. 27, 2011

(65) Prior Publication Data
US 2012/0050736 A1    Mar. 1, 2012

Related U.S. Application Data

(60) Provisional application No. 61/368,053, filed on Jul. 27, 2010.

(51) Int. Cl.
*G01N 21/00*    (2006.01)
*G01N 15/02*    (2006.01)

(52) U.S. Cl.
CPC ................ *G01N 15/0205* (2013.01)
USPC ......................... 356/337; 356/338

(58) Field of Classification Search
CPC ............ G01N 21/00; G01N 15/0205
USPC ................................ 356/335–343
See application file for complete search history.

(56) References Cited

U.S. PATENT DOCUMENTS

| | | | | |
|---|---|---|---|---|
| 4,725,140 A | * | 2/1988 | Musha | 356/336 |
| 5,238,811 A | * | 8/1993 | Fujiwara et al. | 435/5 |
| 5,252,493 A | * | 10/1993 | Fujiwara et al. | 436/526 |
| 2005/0048599 A1 | * | 3/2005 | Goldberg et al. | 435/34 |

* cited by examiner

*Primary Examiner* — Michael P Stafira
(74) *Attorney, Agent, or Firm* — Wolf, Greenfield & Sacks, P.C.

(57) ABSTRACT

The disclosure relates to bioassays, as well as related devices and methods for detecting targets. The targets may be molecules and/or biological products that a user is interested in analyzing to determine information such as their presence and/or concentration in a sample.

13 Claims, 22 Drawing Sheets

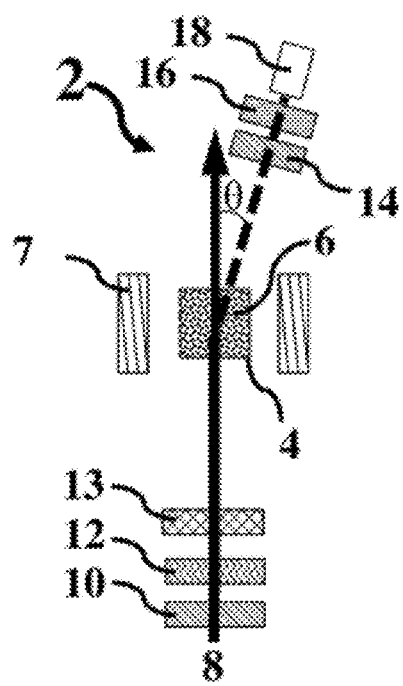
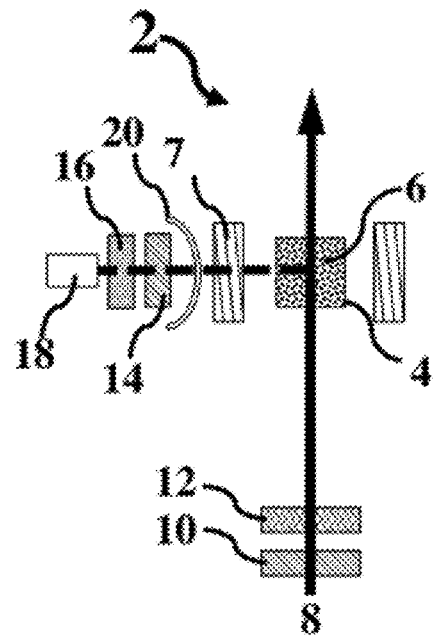
Fig. 1A          Fig. 1B
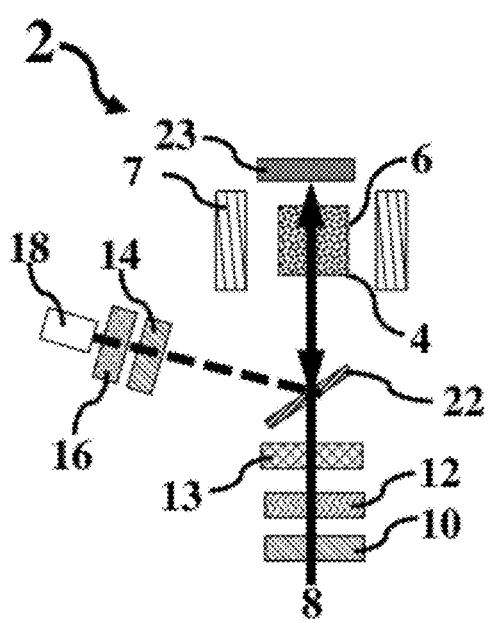
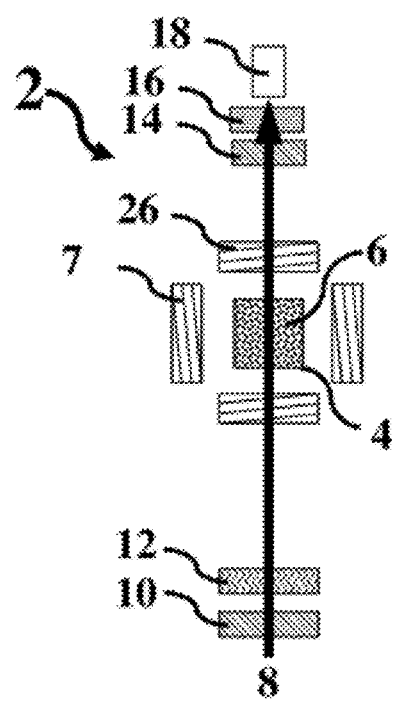
Fig. 1C          Fig. 1D

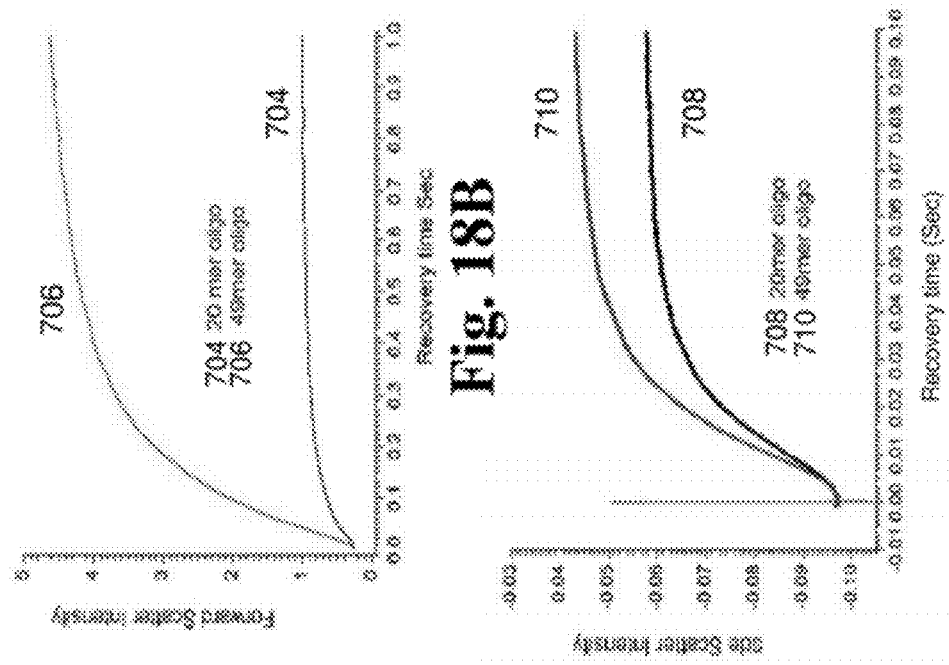
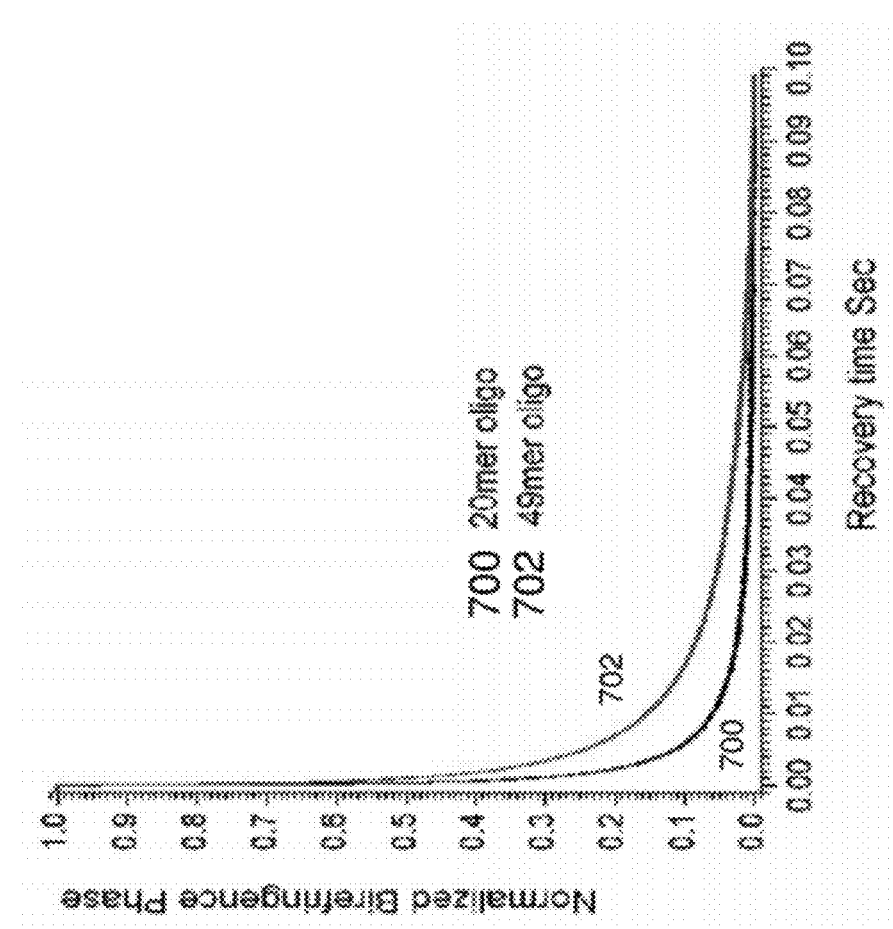
Fig. 18A  Fig. 18B  Fig. 18C

MAGNETIC PARTICLE-BASED BIOASSAYS

RELATED APPLICATIONS

This application claims priority to U.S. Provisional Patent Application Ser. No. 61/368,053, filed Jul. 27, 2010 which is incorporated herein by reference in its entirety.

FIELD

The invention relates generally to the use of magnetic particle-based bioassays, as well as related devices and methods for detecting targets.

BACKGROUND

Bioassays may be used to obtain information about a sample. For example, bioassays are commonly used for detecting the presence and concentration of a substance in the sample. The substance being detected may also be referred to as a "target".

Bioassays can be used in a variety of applications. For example, in some cases, bioassays are used to determine the concentration and purity of a pharmaceutical product as part of a quality control system. Bioassays may also be used for clinical sample analysis to aid in the diagnosis of a disease or condition. Furthermore, bioassays can be used for the purpose of combating bio-terrorism by helping to detect the presence of toxic biological agents within an area. Thus, bioassays are an important and versatile analytical tool that can be used in a variety of industries and settings for multiple purposes.

New types of bioassays, therefore, are desirable, particularly bioassays that are fast, sensitive, and easy to use.

SUMMARY

Magnetic particle-based bioassays and related methods are described herein.

In one aspect, a method for analyzing a sample is provided. The method comprises: providing a sample that includes complexes that comprise one or more magnetic particles bound to a target and applying a magnetic field to the sample to align at least some of the complexes. The method further comprises directing light at the sample and detecting light scattered by the sample.

In another aspect, a bioassay device is provided. The bioassay device comprises a sample area configured to include a sample that includes complexes that comprise one or more magnetic particles bound to a target. The bioassay device further comprises a magnetic field source that is constructed and arranged to apply a magnetic field to the sample area. The bioassay device also comprises a light source constructed and arranged to direct light to the sample area and a detector assembly constructed and arranged to measure light scattered by the sample.

In yet another aspect, a method for analyzing a sample is provided. The method comprises providing a sample that includes unbound magnetic particles and complexes that comprise one or more magnetic particles bound to a target. The method further comprises applying a first magnetic field to the sample for a first duration in a first direction and removing the first magnetic field from the sample. The method further comprises applying a second magnetic field to the sample for a second duration in a second direction substantially perpendicular to the first direction and removing the second magnetic field from the sample. The method further comprises directing light at the sample and detecting at least one of birefringent phase delay in light emanating from the sample and anisotropic light scattered from the sample.

In another aspect, a bioassay device is provided. The bioassay device comprises a sample area configured to include a sample that includes complexes that comprise one or more magnetic particles bound to a target. The bioassay device also comprises a first magnetic field source constructed and arranged to apply a magnetic field in a first direction to the sample area and a second magnetic field source constructed and arranged to apply a second magnetic field in a second direction to the sample area. The bioassay device further comprises a light source constructed and arranged to direct light to the sample area and a detector assembly constructed and arranged to measure at least one of birefringent phase delay in light emanating from the sample and anisotropic light scattering from the sample.

In yet another aspect, a method for analyzing a sample is provided. The method comprises providing a sample that includes unbound magnetic particles and complexes that comprise one or more magnetic particles bound to a target. The method further comprises applying a magnetic field to the sample and removing the magnetic field from the sample. The method further comprises detecting at least one of birefringent phase delay in light that is backwardly reflected from the sample and backscattered light.

It should be appreciated that all combinations of the foregoing concepts and additional concepts discussed in greater detail below (provided such concepts are not mutually inconsistent) are contemplated as being part of the inventive subject matter disclosed herein. In addition, all combinations of claimed subject matter are contemplated as being part of the inventive subject matter disclosed herein.

The foregoing and other aspects, embodiments, and features of the present teachings can be more fully understood from the following description in conjunction with the accompanying drawings. It should be understood that aspects of the invention are described herein with reference to the figures, which show illustrative embodiments in accordance with aspects of the invention. The embodiments described herein are not necessarily intended to show all aspects of the invention. It should be appreciated, then, that the various concepts and embodiments introduced above and those discussed in greater detail below may be implemented in any of numerous ways, as the disclosed concepts and embodiments are not limited to any particular manner of implementation. In addition, it should be understood that aspects of the invention may be used alone or in any suitable combination with other aspects of the invention.

BRIEF DESCRIPTION OF THE DRAWINGS

The accompanying drawings are not intended to be drawn to scale. In the drawings, each identical or nearly identical component that is illustrated in various figures may be represented by a like numeral. For purposes of clarity, not every component may be labeled in every drawing.

FIG. 1A is a schematic representation of a bioassay device including a detector offset at an angle with an associated magnetic source;

FIG. 1B is a schematic representation of a bioassay device including a side scattering detector with an associated magnetic source;

FIG. 1C is a schematic representation of a bioassay device including a detector for back-reflected light with an associated magnetic source;

FIG. 1D is a schematic representation of a bioassay device including a detector with two associated orthogonal magnetic sources;

FIG. 18A is a graph of normalized birefringence retardation phase signals versus recovery time for 20 mer and 49 mer oligonucleotides conjugated to aminated nanoparticles;

FIG. 18B is a graph of forward scattering intensity signals versus recovery time for 20 mer and 49 mer oligonucleotides conjugated to aminated nanoparticles; and FIG. 18C is a graph of side scattering intensity signals versus recovery time for 20 mer and 49 mer oligonucleotides conjugated to aminated nanoparticles.

DETAILED DESCRIPTION

Figure 2:
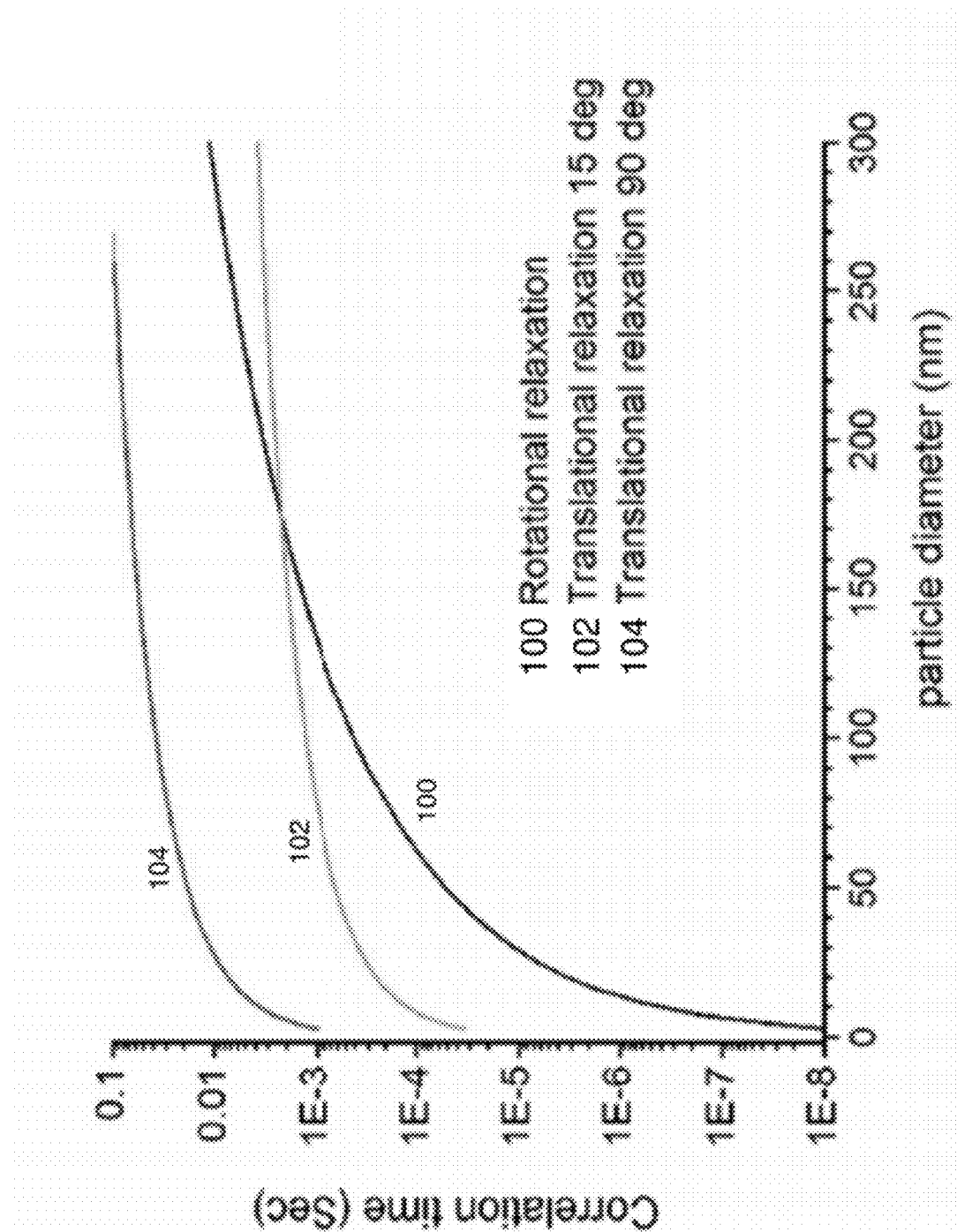
FIG. 2 is a graph comparing Brownian rotational and translational relaxation times and particle diameters.

The following disclosure relates to bioassays, as well as related devices and methods for detecting targets. The targets may be molecules and/or biological products that a user is interested in analyzing to determine information such as their presence and/or concentration in a sample. The bioassays utilize a fluid sample that includes the targets (if present) and magnetic particles. The magnetic particles bind to the targets to form complexes which initially are typically randomly oriented within the fluid sample. The detection methods can involve applying a magnetic field that orients the complexes so that the complexes are aligned with the field. When the magnetic field is removed, the complexes return to their original random orientation. The detections methods further involve directing light at the sample as the complexes are being aligned with the field and/or as they return to their original random orientation, and detecting the resulting scattered light at any angle away from the direction of light propagation through the sample, or phase retarded light emanating at fixed directions from the sample. As described further below, the detected signal may be analyzed to determine the presence of the targets, as well as other information.

FIGS. 1A-1D schematically illustrate different configurations of a bioassay device 2. In these embodiments, the bioassay device includes a sample area 4 of a fluid sample 6 that includes the magnetic particles and targets (if present). As noted further below, the targets (if present) bind to surfaces of one or more magnetic particles to form complexes. The assay may include a magnetic field source 7 configured to apply a magnetic field to the sample area and a light source 8 that directs light into the sample area. A suitable detector 18 is appropriately positioned to detect the scattered light or birefringent light from the sample. In the illustrated embodiments, a polarizer 10, a filter 12, and an optional phase element 13 (e.g., a wave plate) can be positioned so that the light impinging on the sample is polarized and monochromatic. Also, a second polarizer 14 can be positioned so that the light being detected has a desired polarization. A lens 16 may also be provided to collect and focus the scattered light prior to detection.

It should be understood that the bioassay device may include additional components not shown here and that some components (e.g., polarizers, filters, lens) are optional and not used in some embodiments.

A wide variety of samples 6 may be used in the bioassay devices and detection methods described herein. In general, the type of sample depends on the application. Samples include a fluid component in which the target (if present), magnetic particles and complexes are distributed (e.g., suspended). Suitable fluids include saline solutions; body fluids (e.g., blood fractions, whole blood, urine, cerebral spinal fluids); buffers; and impure mixtures. It should be understood that the fluid component may contain other organic, inorganic, or biological materials in addition to the magnetic particles, targets and complexes.

Sample area 4 may have a variety of configurations depending on the application. In general, the sample area is the area of the sample being analyzed. It may be the entire sample, or a portion of the sample. The sample area is selected to allow for application of the magnetic field and performance of the optical measurements described herein. In some embodiments, the sample area is defined by a sample holder that contains the sample. To avoid light refraction resulting from the sample holder which may otherwise interfere with the detection method, in some embodiments, the sample holder may be surrounded by a fluid (not illustrated) that has an index of refraction substantially matched to sample holder to minimize light refraction by the sample holder.

The sample area can be defined by a portion of a larger system. For example, the sample area may be defined by an in-line flow cell, an open collection well, or a closed collection well. In some embodiments, the sample area may be incorporated into a microfluidic system. In some embodiments (e.g., in high throughput applications), the sample area may be incorporated into (e.g., at the outlet, or end, of) a bioreactor, a biological and clinical sample processing station, a robotic sampling device, or a mixing device. In some embodiments, the sample area may be positioned at the end of a chromatography system, microscopic inspection station, or at the end of a columnation system. In some embodiments, the sample area may be a portion of one of the following: a cell culture system, perfused tissue sections, ex vivo samples of extracted cells and fluids, or portions of exposed living organs. Thus, in some embodiments, the sample area may merely comprise a space with access for optical observation and measurement.

The bioassay may be used to detect targets in a variety of applications. For example, suitable targets include molecules and/or biological products such as viruses, bacteria, fungi, cell lines, yeasts, proteins, protein fragments, DNA, RNA, glycoproteins, lipoproteins, carbohydrates, clinical analytes, biomarkers and molecules present in living tissues and cells. It should be understood that other suitable targets are also envisioned.

In some embodiments, the targets may be found in impure collections of mixed biological molecules or products present in colloidal suspensions. Such colloidal suspensions can be encountered in preliminary isolations of viruses, bacteria, and fungus, or in crude isolations of products from cell culture, phage, bacterial, yeast and ribosomal display libraries, as well as in various bioreactors and environmental samples.

As stated above, the bioassays described herein utilize magnetic particles. In some embodiments, it may be preferable to use magnetic nanoparticles. The magnetic particles may have an average particle size of less than 500 nm; in some embodiments, the magnetic particles may have an average diameter of between 1 nm and 50 nm. It should be understood that other sizes are also possible. In some embodiments, the magnetic particles may be formed of a paramagnetic material, superparamagnetic material, as well as ferromagnetic or ferrimagnetic materials. The use of superparamagnetic particles may be helpful in reducing or eliminating aggregation of the particle-target complexes due to the elimination of residual magnetization. Suitable magnetic materials include magnetite and ferrites (e.g., manganese ferrite), amongst others. The use of single domain nanoparticles is particularly preferred, including: cobalt ferrite, zinc ferrite, nickel ferrite and maghemite. Nanoparticles that are simultaneously superparamagnetic and optically active (e.g. double refractive) are particularly preferred. It should be understood that other types of magnetic materials may also be used. In addition to the above, the magnetic particles may also possess an easy axis of magnetization, as would be understood by one of skill in the art. Furthermore, the magnetic particles may possess non-isotropic polarizability at optical wavelengths.

In certain embodiments, the magnetic particles may be capable of anisotropic light scattering. Examples of magnetic particles capable of providing anisotropic light scattering include, but are not limited to: ellipsoidal, rod like, or spindle-shaped ferro and ferromagnetic nanoparticles, including ferrites, magnetite, and maghemite; core/shell particles containing a ferrite core and metal shell; and dumbbell-shaped particles containing a ferrite member and a metal member fused together at a junction.

The targets may be attached to the particles using known techniques. For example, the magnetic particles may be functionalized to include on their surfaces a species that promotes binding to the target. Examples of suitable binding species include receptors or ligands (e.g., antibody, aptamer, generic small organic molecule, peptide, protein, protein fragment, polysaccharide, glycoprotein, nucleotide, or hybridization probe). The binding species are appropriately selected to bind to specific targets.

In some embodiments, a single target may bind with multiple magnetic particles to form a complex. Such multi-particle complexes (or "scaffolds") can have certain advantages in the methods described herein. For example, such complexes can have a relatively large size which can increase light scattering and facilitate detection in some embodiments. Furthermore, multi-particle complexes may reduce the threshold magnetizing fields and decrease the time necessary to orient the complexes in response to a given magnetic field. However, it should be understood that not all complexes include multiple magnetic particles and that complexes including a single magnetic particle may also be used alone, or in combination with complexes using multiple magnetic particles. Similarly, in some applications, it may be useful to allow the magnetic particles to form bridges between targets such that complexes comprise multiple nanoparticles and multiple targets.

In some embodiments, the sample may include a number of unbound magnetic particles in addition to the complexes. Such unbound particles may remain in the fluid sample, for example, suspended along with the complexes. Advantageously, the samples generally do not require prior isolation of the complexes and/or removal of the unbound particles for the detection methods described herein. Furthermore, advantageously, the bioassay devices and methods described herein typically do not require introduction of additional labels which, for example, need to be removed prior to the detection step. Thus, in these embodiments, the bioassay can be considered "label free".

In some embodiments, after target detection, the complexes may provide the means to isolate and capture the target. Thus, in these embodiments, the bioassay may be used for other purposes in addition to detection including capture and isolation. For example, the bioassay may be used to detect and capture viruses and bacteria, and to screen for expression of recombinant protein libraries in bacterial and yeast expression systems.

Magnetic field source 7 applies a magnetic field to the sample area. Any suitable magnetic field source may be used. For example, the source may be an electromagnetic source and may comprise a pair of Helmholtz coils or an extended solenoid coil. Other sources of magnetic fields may also be suitable.

Typically, it is preferable for the source to provide a relatively homogenous magnetic field to the sample area. That is, the applied field is substantially uniform in magnitude across the sample area. The magnitude and duration of the applied field are generally selected to sufficiently orient the complexes within an appropriate time. The magnitude of the necessary time duration scales with the complex hydrodynamic volume and is inversely proportional to the effective magnetic moment of each particle and the number of particles that bind to the complex. Typical magnitudes for the applied fields include 50 to 400 Oersteds (gauss) and typical time durations are 1 microsecond to 5 seconds. In addition, in some embodiments, fast field switching may be desired. Rise and fall times less than ten microseconds may be particularly preferred. The magnetic field can be applied in a direction that is substantially perpendicular to the propagation of light through the sample area from the light source, as described further below.

In some embodiments, as shown in FIG. 1D and described further below, the bioassay includes a second magnetic field source 26. The second magnetic field source may be any of the types described above, and may be oriented to produce a magnetic field perpendicular to the first magnetic field. As described further below, in some embodiments, the second magnetic field source may apply field at different times (e.g., before or after) than the first magnetic field source. In some of the embodiments, the second magnetic field may be useful for methods that involve detecting phase modulated light.

Light source 8 of the bioassay provides light to the sample area. Any suitable light source may be used including a laser, an LED, and a light bulb, among others, depending on whether polarized or unpolarized detection is desired. Preferable wavelengths depend on the target selected and the composition of the fluid. In general, the wavelength is chosen where the sample exhibits little light absorption. As the suspending fluid is generally water, wavelengths between 200 nm-1100 nm may frequently be used. If scatter detection is used, shorter wavelengths may be preferred to maximize sensitivity. Otherwise, wavelengths may be chosen on the basis of avoiding light absorption by the target and interfering substances present in the sample. Preferred wavelengths may take advantage of the optimal optical activity of the nanoparticles and/or targets.

The path of light propagation through the bioassay shown in FIG. 1A is indicated by the arrow. As shown, the light source 8 may be in line with polarizer 10 and filter 12, and phase compensator 13 (e.g., a wave plate including ¼λ, ½λ wave plate). The polarizer and filter may be included so that the light provided to the sample area may be polarized and monochromatic which can be advantageous for the detection methods described herein. The phase compensator may also minimize light leakage into the detector, in some embodiments. It should be understood that the polarizer, filter, and phase compensator are not necessary in all embodiments. In some embodiments, a variable phase compensator may be included to correct for the intrinsic birefringence of a sample holder in the sample area. For example, the variable phase compensator may be a liquid crystal variable phase delay compensator.

As noted above, the bioassay includes detector 18 for detecting scattered light or, in some embodiments, phase retarded light. In general, any suitable detector may be used. For example, the detector may be a photodetector, a high speed photodiode, an Avalanche photodiode, a photomultiplier and a CCD camera (including an intensified CCD camera). The detector may include, or be coupled to, appropriate electronics (e.g., pre-amplifier with/without offset, lock-in amplifiers, boxcar averagers, correlators, etc) for electronic processing of the detected signals.

As shown in FIG. 1A, the bioassay may include polarizer 14 and lens 16 within the pathway of scattered light, or phase retarded light, before the detector. Lens 16 may optionally be provided to appropriately collect and focus the light prior to detection.

As light passes through the sample area it may undergo different types of light scattering (including forward light scattering, side light scattering, backward light scattering (i.e., backscattering) and/or phase delay due to birefringence (i.e., birefringent phase delay) in the sample. The birefringent phase delay may be measured from forward directed light and/or backwardly reflected light from the sample. In some embodiments, the light may undergo anisotropic light scattering due to anisotropic light scattering properties of the targets or particles present in the sample area. Depending on the type of light scattering being detected, the detector and related components (e.g., polarizer, lens) may have different arrangements. For example, FIGS. 1A-1D illustrate different detector arrangements in which the detector (and related components) is aligned and arranged at different orientations with respect to the path of light propagation through the sample area, as described further below.

The bioassay device in FIG. 1A is configured to detect light scattering from the sample at an angle θ. In such a configuration, the detector is aligned and arranged at an angle θ from the path of light propagation through the sample indicated by the arrow. Generally, when forward light scattering is being detected, angle θ may range from 5° to 20°. However, in some embodiments when forward light scattering is being detected, angle θ may be less than 5° or greater than 20° as the current disclosure is not limited in this manner. When θ is configured between 45° and 135° the detector is positioned to intercept side scattered light. When θ is configured to be greater than 135°, the detector is positioned to intercept back scattered light.

The bioassay device in FIG. 1B is configured to detect side light scattering from the sample as indicated by the dashed lined. In this illustrated embodiment, the detector is aligned and arranged at an angle substantially 90° from the path of light propagation through the sample. While an angle of 90° has been illustrated, it should be understood that the detector assembly may be arranged at other angles including between 45° and 135° to detect side light scattering. In some instances, a cylindrical lens 20 may be provided between the sample and polarizer 14 to focus the side scattered light from a line source prior to its entry into the detector.

The bioassay device in FIG. 1C is configured to detect back light scattering at 180° from the sample. In this embodiment, the bioassay device may include a beam splitter 22 located between filter 12 and the sample area. The beam splitter (pellicle, for example) may be aligned with and oriented at substantially 45° from the path of light propagation through sample area 4 indicated by the arrow. While the beam splitter has been depicted at 45°, it may be oriented between approximately 25° and 135° with respect to the path of light propagation through the sample area. The beam splitter may direct a beam of back scattered light through the polarizer 14, lens 16, and detector 18.

While back light scattering may be conducted on such an arrangement, the embodiment depicted in FIG. 1C may be especially suited to measuring the birefringence phase delay if a light reflector 23 is positioned at the outlet of the sample area 4 such that it directs the outward propagating light beam back along its original path through the sample into the beam splitter and subsequently into detector 18. The advantage of this configuration is an increased (double) path length through the sample area due to reflections at the reflector. Additional reflections of the light beam causing the light to cross the same path through area 4 may be implemented by adding a second optional beam splitter in the embodiment of FIG. 1C. Temporal variations in the index of refraction of the sample will cause temporal variations in the phase delay as measured by detector 18.

The bioassay device in FIG. 1D is configured to detect birefringent phase changes in light along the forward propagating path from the sample. The bioassay device in this embodiment may include a polarizer 14, focusing lens 16, and detector 18 substantially aligned and arranged along the path of light propagation through sample area 4 (i.e. approximately $\theta=0$).

As discussed above, the detection methods described herein can involve subjecting randomly oriented complexes to a magnetic field of sufficient strength and duration such that at least some (e.g., at least 50%) of the complexes substantially align with the field. That is, at least some of the complexes orient to the direction in which the magnetic field is applied. In some embodiments, at least 75% of the complexes substantially align with the field; in some embodiments, at least 85%; and, in some embodiments substantially all of the complexes substantially align with the field. The requisite strength and duration of the field may be determined based upon a number of factors including the number of magnetic particles that bind to the target, the size of the target, and the average particle magnetic moment. After the complexes have reached a steady state of alignment with respect to the applied magnetic field, the field may be removed (also known as "quenching"). Upon removal of the magnetic field, and as described above, the complexes relax back to their original random orientations.

The complexes and particles orient (when the field is applied) and relax (when the field is removed) by rotational and translational diffusion through the sample fluid. Due to the difference in size, moment of inertia, and/or diffusion rate constants, between the particles and complexes, the smaller magnetic particles may orient and relax more quickly during both the application and quenching of the magnetic field in comparison to the larger complexes. The orientation and relaxation processes noted above may be characterized using the light detection-based techniques described above (e.g., forward light scattering, side light scattering, backward light scattering, and/or birefringence phase delay). In some instances the detected signal may include orientation/relaxation processes due to orientation/rotational relaxation, translational orientation/relaxation, or both. In some embodiments, the detected signal may be analyzed to determine a probability distribution of species (e.g., complexes, unbound magnetic particles, etc.) based on the distribution of rotational rates within the sample. The probability distribution may then be used to identify populations of species within various size ranges. The size distribution may then be used to identify the presence and concentration of a target. In some embodiments, the orientation and relaxation constants (which are respective measure of the time it takes to orient and relax) may be determined and changes relative to the orientation and relaxation constant of the unbound particles may be indicative of a the presence of a target. The relaxation measurements thus obtained may be used to characterize the target size and/or shape (from the relative scattering anisotropy with complex orientation), which may help to enhance the bioassay specificity and confidence limits. The orientation measurements may be used to characterize the magnetization properties of the complexes. These may be used to determine the number of nanoparticles that bind to target, producing the scattering complexes By selecting a reproducable set of initial alignment conditions, it is possible to measure the rotational diffusion rates of the complexes by measuring the rate change in light scatter with time. If targeted complexes bind to magnetic particles, they can be rotated into preferred alignment by application of a magnetic field. Subsequent to field quenching, the magnetic complexes randomize their orientation by collisions with the fluid in which they are suspended. If the target particles or the magnetic particles that bind to them possess intrinsic optical anisotropy (due to composition and/or shape), they will scatter light with different intensity depending on their orientations. Alternatively, inclusion of magnetic particles possessing an intrinsic optical anisotropy (such as birefringence) permits targeted complexes to be made optically anisotropic and thus scatter light with different intensity depending on their present orientations, regardless of whether optical anisotropy exists within the target itself. By observing the relaxation, and/or orientation, of the complexes due to application and removal of the magnetic field using the above noted optical techniques, changes in the relaxation and/or orientation rates may be observed. Changes in the associated rate constants may be associated with the presence (i.e. detection) of a targeted species in the sample. The complex will have a longer relaxation time than the unbound magnetic particles, so generally, an increase in the relaxation time may correspond to binding of magnetic particles to targets.

A comparison of the rotational relaxation time and the translational relaxation times measured at 15° (forward scatter) and at 90° (side scatter) for spheres of varying diameter is shown in FIG. 2. The rotational times were calculated from the Debye-Einstein-Stokes equation for rotational diffusion. The translational diffusion times were calculated from the Einstein-Smoluchowski equation for translational diffusion and are seen to depend on the square of the scattering wave vector, unlike the rotational times. As shown in FIG. 2, the rotational relaxation time, corresponding to curve 100, is a more sensitive indicator of cluster size than the translational relaxation time corresponding to curves 102 and 104 measured at 15° to 90° respectively. Thus, in general, the rotational diffusion coefficient may be more sensitive to differences in the size of the complex. In some embodiments, the measurement may look at scattering from the magnetic nanoparticles, the target, and/or the complexes. Frequently, the rotational diffusion rate constant is several orders of magnitude faster than the translational diffusion rate constant, and therefore the rotation rate determines the overall rate change of scattering amplitude. If the rotational rates show a decrease in value from their values in a control containing no targets, the bioassay may identify the presence of the targeted species in the sample since the unbound particles have faster relaxation rates. Because the magnitude of the values of the rotational and translational diffusion coefficients confers information of the physical dimensions of the entire complex, the relaxation information can be used to evaluate the specificity of the bioassay and increase confidence in its results.

When measurements are performed in impure mixtures, or with unbound particles, the modulated light scattering associated with these measurements may be immune from the usual interferences from other scattering species present in the sample because the scattering associated with the other species are not synchronous with the magnetic field modulation. In some embodiments, the complexes may include multiple binding sites and may form a multi-particle complex (or "scaffolds"). Light scattering from multi-particle complexes may be distinguishable from scattering from unbound particles by the angular dependence and the time-course of the relaxation. In some embodiments, the measured light scattering may be entirely due to scatter from the complexes. When the target is sufficiently large in comparison to the particles, scattering from the complex may offer an increased scattering signal due to the increased scattering area of the complex versus the individual nano-particles. Similarly, targets binding with multiple particles may exhibit an increased scattering signal as compared to targets binding with single particles. Consequently, due to the increased scattering signal from either the larger scattering area of the complex, or scattering from multiple particles bound to individual targets, the current bioassay may exhibit an increased sensitivity and resolution of target size.

In certain embodiments, a pulsed magnetic field may be applied to the sample with an appropriate magnitude, direction, duration, and frequency to rotate the complexes to produce substantial alignment with the applied field. Fast quenching of such fields allows measurement of the rotational relaxation of the complexes to be made. Cyclic repetition of such alignment and relaxation events may be used to provide measurements of average relaxation and orientation dynamics. In one embodiment, a pulsed homogeneous magnetic field, may be applied to the sample along a direction perpendicular to the direction of propagation of the monochromatic, polarized light beam. The magnetic field may be applied for a time that enables the ensemble average electric polarization vector of the collection of particles and complexes to substantially re-align in a direction corresponding to the direction of the applied magnetic field. Under these circumstances, the particles and complexes may align in the direction of the field during the magnetic field on cycle (STEP ON phase), and reorient to random orientations by rotational Brownian relaxation during the off cycle (STEP OFF phase). This may result in a measurable change in the light scatter intensity from the ensemble that returns to its original steady state intensity in a time characterized by the sum of rotational and translational relaxation times of the complexes. The translational relaxation component may be eliminated by averaging the relaxation signal over several periods of field activation and quenching. Such a bioassay may produce enhanced signal to noise when the signals obtained from multiple pulse sequences are averaged over repeated magnetic cycles with proper regard to their place in the time sequence, as measured relative to a field switching event.

In an alternative embodiment, the magnetic field may be sinusoidally modulated at frequencies below a critical frequency that is constrained by the moment of inertia and hydrodynamic volume of the complexes. In this case, in order to maintain a continuous response, it may be desirable to apply the sinusoidal modulation in the presence of a bias steady state magnetic field oriented orthogonal to the modulating sinusoidal field. If the steady-state field has a magnitude much greater than the oscillating field, the aggregate cluster may precess about the steady-state field direction at all frequencies below the critical frequency and give rise to a scattering amplitude of oscillating frequency.

In some embodiments, the sample being analyzed may contain a distribution of targets of different sizes. Different angles of scatter may be used to select and weigh, to varying proportions, the different size components of targeted species present. The spectral deconvolution of the relaxation time course obtained at different angles of scatter may be used to determine the weight proportion given to a particular size fraction at the measured angle of scatter.

In other embodiments, the angle of scattering may be used to provide size differentiation of targets. In general, the single particle scattering cross section function may emphasize the scattering contributions from larger complexes at small scattering angles over the contributions from smaller complexes at the same angle. Thus larger targets and aggregates produced by linking smaller targets together with targeting receptors may be detected with greater weight at small angles (e.g., for $\theta \leq 15°$) rather than large angles (e.g., $\theta = 90°$). In systems containing heterogeneous size distributions, relaxation signals obtained by small angle scattering measurements may, in general, exhibit longer relaxation times than the species detected at higher angles. The examples, presented below, indicate that in addition to temporal discrimination of size within heterogeneous populations of ligand-receptor complexes, it may also be possible with light scattering (unlike birefringence) to discriminate target size based on scattering angle. Measurements based on the birefringence inherent in the crystal structure of certain particles, on the other hand, results in signals that weigh equally all size components in the sample and reflect in the normalized time course of relaxation, the fractional number of birefringent particles relaxing at a particular rate.

The bioassay devices and methods may also be used to determine the concentration of targets by comparison with a calibration. In one embodiment, the concentration may be determined by the variation of the difference between the absolute intensity of scattering between the maximally aligned clusters and the randomly oriented clusters. A calibration may be obtained with independently measured spiked levels of target. The difference may preferably be measured from the scatter intensity difference obtained just prior to field quenching and the scatter intensity obtained after the relaxation transient has leveled off. This calibration may be affected by the particular wavelength, sample irradiance, scattering angle, and magnetic field strength and duration of the aligning field.

The bioassay devices and methods may also be used to determine the net magnetization and magnetic moment of the target complex from the time course of complex orientation (STEP ON phase) as shown in Example 1. From these values one can estimate the net number of nanoparticles binding to the target complexes if the net magnetization per nanoparticle is known and superparamagnetic magnetization of a collection of nanoparticles scales with the density of bound nanoparticles. Thus knowledge of nanoparticle binding density may be used to evaluate the minimum number of possible ligands present in, or on, the target. In order to perform such a measurement, the time required to orient the complexes for a variety of different magnetic flux densities from the inception of the STEP ON phase of field modulation (during which there is a transition from maximal random orientation) to maximum alignment of the complexes within the same STEP ON phase may be measured. The measurement may coincide with the minimum measurable time between extreme (stationary) levels of sample light scatter during the period of field modulation. The hydrodynamic volumes of the target complexes may also be measured (from the time course of relaxation during the STEP OFF phase of field modulation). Subsequently, the ensemble average particle number per complex may be calculated from the measured rotational orientation time using the hydrodynamic volume and the value of magnetic flux density used to align the complexes.

In some embodiments, it may be advantageous to create aggregate complexes which may have larger aggregate volumes and may be formed by either: chemical amplification or polymerization; binding to multiple particle receptors; bridging multiple complexes together in networks connected by multiple particle bridges; or other applicable processes. The growth kinetics of such aggregates may be determined by measuring rotational rate changes as a function of time after mixing ligand particles and their precursors, and receptor particles together. This measurement may provide real time evaluation of the rate of product amplification based on volume accretion, rather than mass change. In some instances, different aggregate clusters may present a distribution of rotational relaxation rates present in the sample. The different elements of the distribution may be sorted into different ranges of cluster size by performing an inverse Laplace transform on the normalized relaxation decay curves. Example 5 teaches the use of magnetic field modulated birefringence phase changes and anisotropic light scattering for monitoring the generation of nucleic acid polymers during isothermal amplification reactions.

In the above detailed bioassay, the minimum yield of targeted ligands may be determined as a function of time by calculating the product of the ensemble average number of particles (n) binding to each ligand cluster by the number (N) of ligand clusters. The number of particles (n) binding to each ligand cluster may be determined as detailed below. The number of ligand clusters (N) in the sample is obtained from measurements known to those familiar with the art, including, for example, the autocorrelation of light intensities in the absence of field modulation.

In one embodiment, the device of FIG. 1C may be used to measure the generation of product in isothermal nucleic acid amplification reactions in real-time. In addition to the magnetic particles, the sample may include primers, substrates, and enzymes for isothermal nucleic acid amplification that are capable of replicating a portion of template nucleic acids. The magnetic particles may also include one or more hybridization probes chemically coupled to them. After the application, and subsequent removal, of the magnetic field at least one of the birefringent phase delay in light that is backwardly reflected from the sample and/or anisotropic scattered light may be measured to determine a relaxation characteristic of the sample. The reaction may be monitored by multiple relaxation measurements at different time points as the reaction proceeds.

In another embodiment, the device of FIG. 1C may be used to measure and screen the quality of recombinant protein expression systems with respect to binding targeted ligands. The magnetic particles may have one or more target ligands chemically coupled to them. In addition, the sample may further include cells, or cell fragments, possessing protein expression systems or systems that express membrane embedded, recombinant, proteins. After the application, and subsequent removal, of the magnetic field at least one of the birefringent phase delay in light that is backwardly reflected from the sample and/or anisotropic scattered light may be measured to determine a relaxation characteristic of the sample.

In certain embodiments (FIG. 1D), a second magnetic field pulse may be supplied from the second magnetic source 26 which may be coordinated to operate with the first magnetic source 7 in such a manner that when current flows through one, the other is dormant. The timing of pulses may be as follows. The first magnetic source 7 may remain on for a time sufficient to substantially align the complexes. The second magnetic source 26 may subsequently turn on and produces a reorienting magnetic field for a much shorter timed interval. The shorter interval may be sufficient to reorient the unbound particles present in the sample in the direction along the light propagation vector. The particles that are encumbered by virtue of being bound to a target cannot reorient fast enough to respond to the second pulse and thus continue to relax at a rate determined by their hydrodynamic volume. Meanwhile, the smaller unbound particles may substantially reorient in the direction of the second magnetic field thus substantially canceling the contribution to birefringence phase delay and light scattering. The timing for each pulse may be determined as would be apparent to one of skill in the art. After the second magnetic pulse, all magnetic fields may be quenched. The polarized, undeflected light signal may be measured as a function of time, with a time origin t=0, coinciding with the quenching of the field from the first magnetic source. Birefringence phase delay and light scatter signals acquired after the second realigning pulse may be substantially due to the complexes. Furthermore, these signals may show substantially reduced or entirely eliminated contributions from unbound particles. The signals acquired before the second field pulse may represent the birefringence and/or light scatter originating from both the complexes as well as the unbound particles.

To determine the fraction of unbound particles in the mixture the roles of the first and second magnetic sources, 7 and 26, may be reversed. For instance, the second magnetic source 26 (applying a homogeneous magnetic field along the direction of light propagation) may be switched on first, for a duration sufficient to achieve alignment of all particles, bound and unbound. The second magnetic source 26 may then be switched off and immediately the first magnetic source 7 may be switched on. The first magnetic source 7 may remain on long enough to align the unbound particles. Both magnetic sources may then remain off while relaxation data is collected.

The following examples are provided for illustration purposes and should not be considered limiting.

EXAMPLES

Example 1

Determination of $<\mu>$ for Carboxy-Dextran Maghemite Particles

Figure 4:
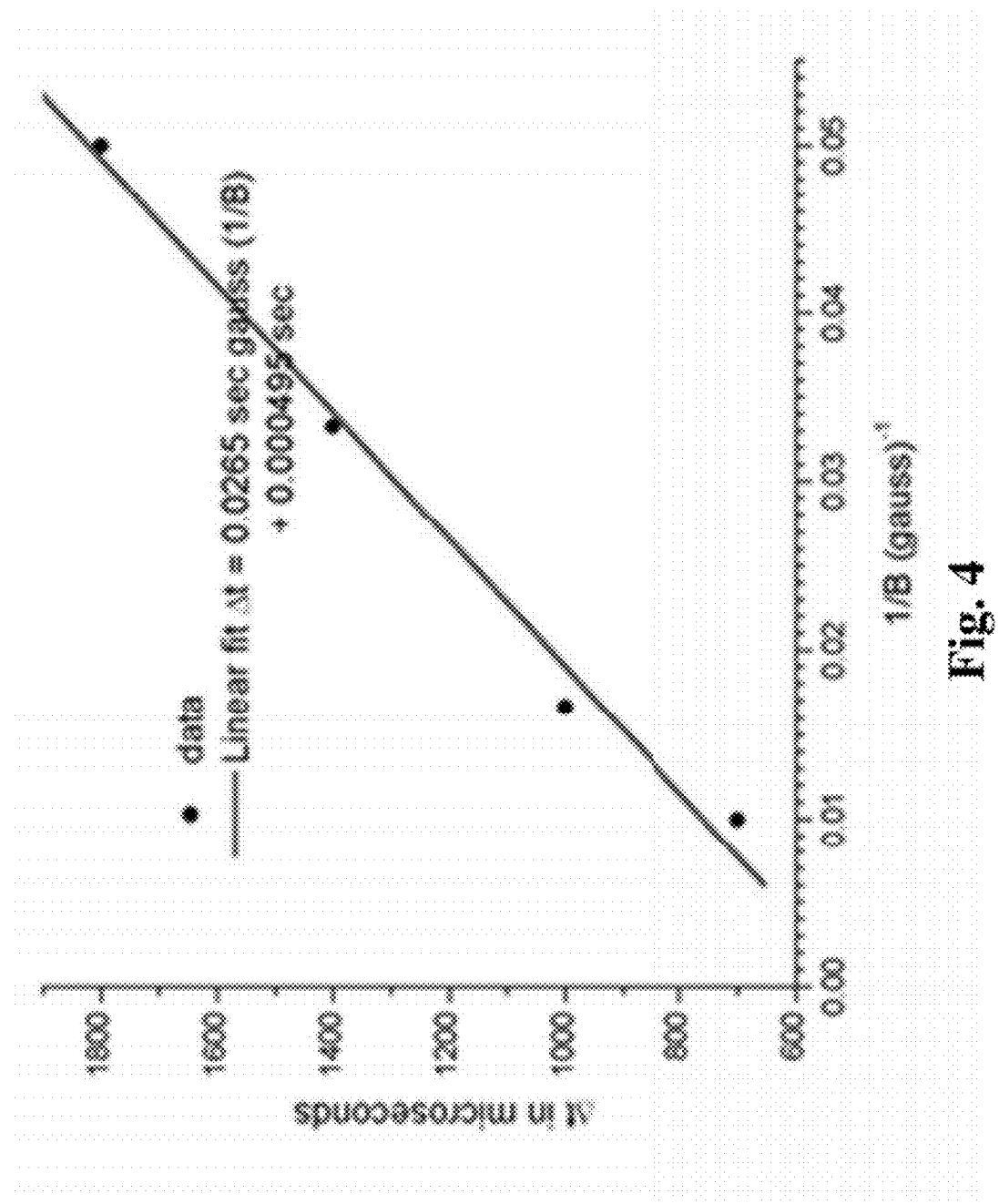
FIG. 4 is a graph comparing particle orientation time ($\Delta t$) versus inverse of the magnetic flux density ($1/B$)

Birefringent nanoparticles (Meito Sangyo's ferucarbotran DDM128N) were used to see the effects of varying orienting field strength B on the time required to achieve maximal particle alignment. Particle alignment toward the field was measured by determining the birefringence phase shift as a function of time (Step On phase) after the field was switched on. The shift was measured using the system of FIG. 1A (with the detector polarizer and phase plate set to minimize light transmission with the sample in place and the field off). A plot of the variation of $\Delta t$ vs $1/B$ is shown in FIG. 4.

The theory describing the angular kinetics of the orienting clusters has been originally described by Langevin. On the assumption that inertial forces acting on the complexes are negligible, the magnetic torque acting on each complex opposes viscous forces exerted by the supporting fluid and fluctuating impulses due to collisions with fluid. A number of theoretical studies have been published demonstrating generalized methods that provide the solution of the time course for the stochastical averages of the orientation parameter <cos ψ>(t), and its various statistical moments and time derivatives. In the present example ψ describes the angle between an axis of anisotropy within the scattering complex and the field direction. The angular brackets represent ensemble averages.

A solution of the one dimensional Langevin equation under conditions of negligible inertia shows that the mean time required to align the complexes (such that <ψ>~0) from purely random orientation is inversely proportional to the magnetic flux density (B) according to:

$$<\Delta t> = const(<\Delta \Psi>) \frac{sV_h\eta}{<\mu>B} \quad (1)$$

Here <μ> represents the ensemble average of the magnetic moment of the magnetic particles, s is a shape parameter (s=3 for a sphere), $V_h$ is its hydrodynamic volume, and η is the dynamic viscosity of the supporting fluid. On the assumption that substantially all aligning particles achieve a final average orientation <ψ>=0 from a starting random orientation where <ψ>=π/2, one may calculate const(<Δψ>)=0.3.

A least squares linear fit to the data of FIG. 4. yields a slope of 0.0265 sec gauss. Measurement of the birefringence decay transient after the field is switched off indicated that the average particle volume was $V_h$=5.1×10$^{-26}$m$^3$. Thus the average magnetic moment <μ> of the particle distribution that responded to the applied field was calculated to be 1.91× 10$^{-24}$ Joule/gauss from eq. 1. This is very close to the anticipated value of <μ>=1.96×10$^{-24}$ J/gauss based upon the literature values of M=60 emu/gram for maghemite. With this value of <μ> having been confirmed, it should therefore be possible to analyze the kinetics of complex orientation and back out the number of nanoparticles binding to each complex.

The usefulness of this is seen in the example of an aggregate complex comprising magnetic particles and target. As nanoparticles aggregate and bind to the target, they add to the magnetic moment of the cluster and contribute to the net magnetization that is needed to rotate the complex in a field of fixed intensity B. The maximum number of nanoparticles that bind to the complex (absent the interparticle magnetic interactions that may be active when the magnetic field is applied) is determined by the number of accessible ligands on the target. If the average number of nanoparticles n binding to the complex and <μ> is their average magnetic moment, then μ=n<μ>L(μB/$k_B$T) is their net effective magnetic moment. Here L(μB/kBT) is the Langevin function, well known to those skilled in the art. Substituting this value for μ in eq 1, a plot similar to that in FIG. 4 may be used to calculate n. This value of n represents a lower limit on the ligand density of the target cluster, as it generally requires more than one ligand to bind a magnetic particle to its target. However, the approximation may be improved as one substitutes smaller magnetic particles until the Neel limit is reached.

Example 2

Relaxation Rates Measured by Birefringence and Light Scattering of Magnetically Oriented Vesicular Stomatitis Virus/Maghemite Np Complexes Field modulated light scattering provides an alternate method for detecting viruses that may offer additional information and benefits compared with conventional immunoassays utilizing optical labels that require additional processing steps. A vesicular stomatitis virus (VSV) was used as a model viral target. VSV is a prototypic rhabdovirus with a bullet-shaped morphology that has been used extensively to study virus entry due to the ability to incorporate heterologous viral glycoproteins into the virion membrane, resulting in the generation of VSV pseudotype particles. For these bioassays, maghemite nanoparticles were decorated with mAbs specific for either the New Jersey (mAb VIII) or Indiana (mAb I1) serotypes of VSV. Titrating virus into a 1 ml volume, it was determined that the signal to noise varied linearly with the applied magnetic field in the range of field flux up to 100 G. With an operating field of 80 G and an interrogated volume of 50 µl, a limit of detection (LOD) of 50 plaque-forming units (pfu) was achieved in an irradiated volume of 50 1 by birefringence measurements.

Figure 3:
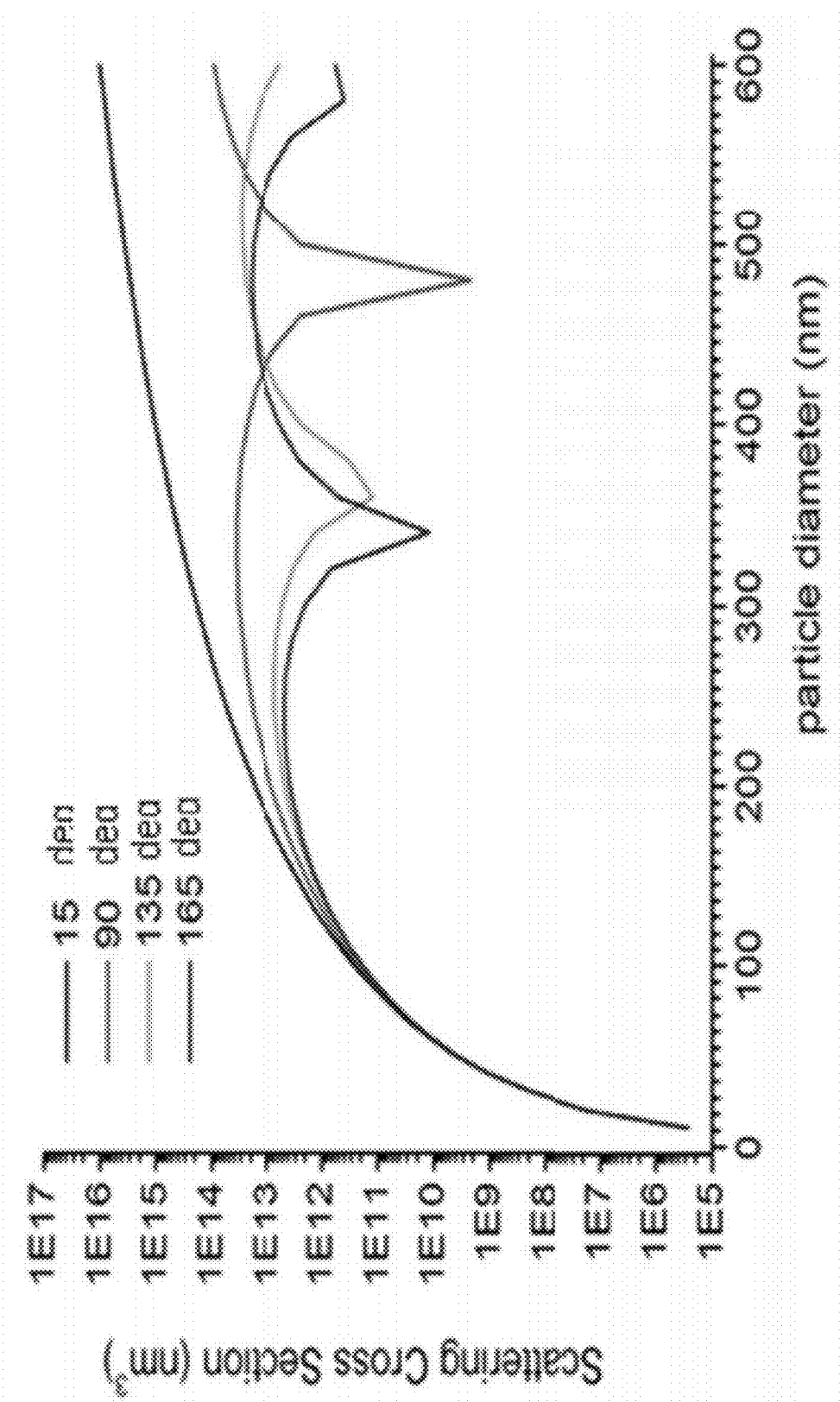
FIG. 3 is a graph comparing threshold particle number detection versus particle diameter for various scattering angles.

FIG. 5 compares the birefringence, side and forward light scatter collected from 10$^4$ pfu/ml VSV in the presence of 10$^{10}$ Staphylococcal protein G nanoparticles/ml and 8 µg/ml I1 MAb. The three sets of spectra were obtained simultaneously during the step off phase of pulsed field modulation. The orientation field had been applied for two seconds and was followed by rapid quenching (within 10 µsec). The field remained off for 8 seconds during which the birefringence phase retardation and scatter signals were collected. Signals were averaged during ten repetition cycles. The three data sets indicate distinctly different ranges of time recovery dynamics. Normalized birefringence phase shows the fastest overall recovery, with side scattering showing the second fastest and forward scattering the slowest recovery. The differences in scatter signals must originate in the angular dependence of the scattering cross sections for individual complexes. This term has the effect of producing unequal spectral weighing for complexes of equivalent size at forward and side angles of scatter as shown in FIG. 3. For size heterogeneous complexes, larger complexes scatter more predominately in the forward, rather than side directions. Thus the larger complexes of a distribution will be given greater spectral weight in the forward scatter direction than in the side direction. In birefringence spectra from maghemite nanocrystals, these same complexes will be given weight equal to the number ratio of magnetic particles that bind to the target and ratioed proportionately to the total number of complexed and uncomplexed magnetic particles in the sample.

Therefore, field modulated forward and side light scatter can be used to provide enhanced amplification factors for particles of greater volume clusters in size heterogeneous samples compared to the uniform detectability of all magnetic particles in birefringence spectra. This fact might be advantageously used to detect trace amounts of target. If the resulting cluster sizes of nanoparticle-target complexes are sufficiently larger than the uncomplexed capture particles, forward scattering will weigh the bound fraction greater than the unbound. The scattering cross section from a single scattering cluster in the Rayleigh-Gans approximation may be used to determine the weighing factor in example 1. It may be noted that a disproportionately greater intensity of scattering in the forward direction occurs for complexes of a diameter greater than 100 nm than for particles smaller than 100 nm.

Phase Function Approach for Separating Mixtures of Exponential Decays

Considering that the virus binding fraction is often only a small fraction of the total number of nanoparticles under observation (in the example of low virus load), it is expected that the fractional change in birefringence phase signals upon virus binding may be small compared with the birefringence phase signal from unbound nanoparticles. Fortunately, the rate change upon virus binding can be very large. The result is to greatly extend the relaxation curves for birefringence phase delay. It has a similar temporal response in the signal dynamics observed by light scattering as well. Therefore the indication of virus binding often presents as a finite change in the temporal window that sees no change in the absence of virus. The overall variation in the signal amplitude within this window derived by light scattering measurements is viewed as an aggregate measure of the amount of virus binding to the nanoparticles. The location of this window in frequency space is viewed as a reflection of the accretion size of the virus-nanoparticle complex. Higher rotation rates reflect faster rotating, hence smaller, complexes, slower rates reflect slowly rotating, hence larger, complexes.

Numerous mathematical formulations have been discovered to extract relaxation rates from complex mixtures of dynamic relaxation processes. Recently, Y. Zhou & X. Zhuang developed a phase function approach for separating components of mixtures in exponential decays which was used in the current experiments to help characterize the size distribution of capture particles as they bind to virus using both birefringence and scattering data.

To compare the fraction of nanoparticles involved in virus capture from both birefringence and scattering data, the signals were first normalized over the interval from t=0 to t=$t_{max}$, where $t_{max}$ represents an arbitrary time after field quenching when the signal amplitude has stabilized, i.e. d<signal>/dt~0. The relaxation curves were interpreted as describing a time distribution of particle orientations that changes with time for an ensemble averaged signal p(t). p(t) may have a value equal to one when all of the (measurable) particles are maximally aligned with the field and zero when all the particles interrogated are randomly aligned. That is, p(t) was identified as a probability of particle alignment in the direction of the quenched magnetic field. The inverse of the relaxation times, are the relaxation rate constants of the size heterogeneous clusters given by their rotational relaxation times. The Stokes-Einstein equation relates the rate variable to a size variable, i.e. the hydrodynamic volume.

A common way to describe the distribution of rate constants is by another probability density, π(k), which is related to p(t) by a Laplace transform. The evaluation of π(k) is formally obtained from the inverse Laplace transform of p(t). It is frequently found, however, that the inverse Laplace transform of time domain data is unstable. Zhou & Zhuang solved the instability problem and permitted a generalized solution that does not require the imposition of arbitrary constraints on the solutions. Software was provided by the Zhuang lab at Harvard and used to extract the probability density distributions for reorientation rate constants due to Brownian motion of the nanoparticle conjugates before and after attachment to VSV. When combined with the Stokes-Einstein relation, this analysis provides the size distribution of capture complexes under various experimental conditions.

Figure 5A:
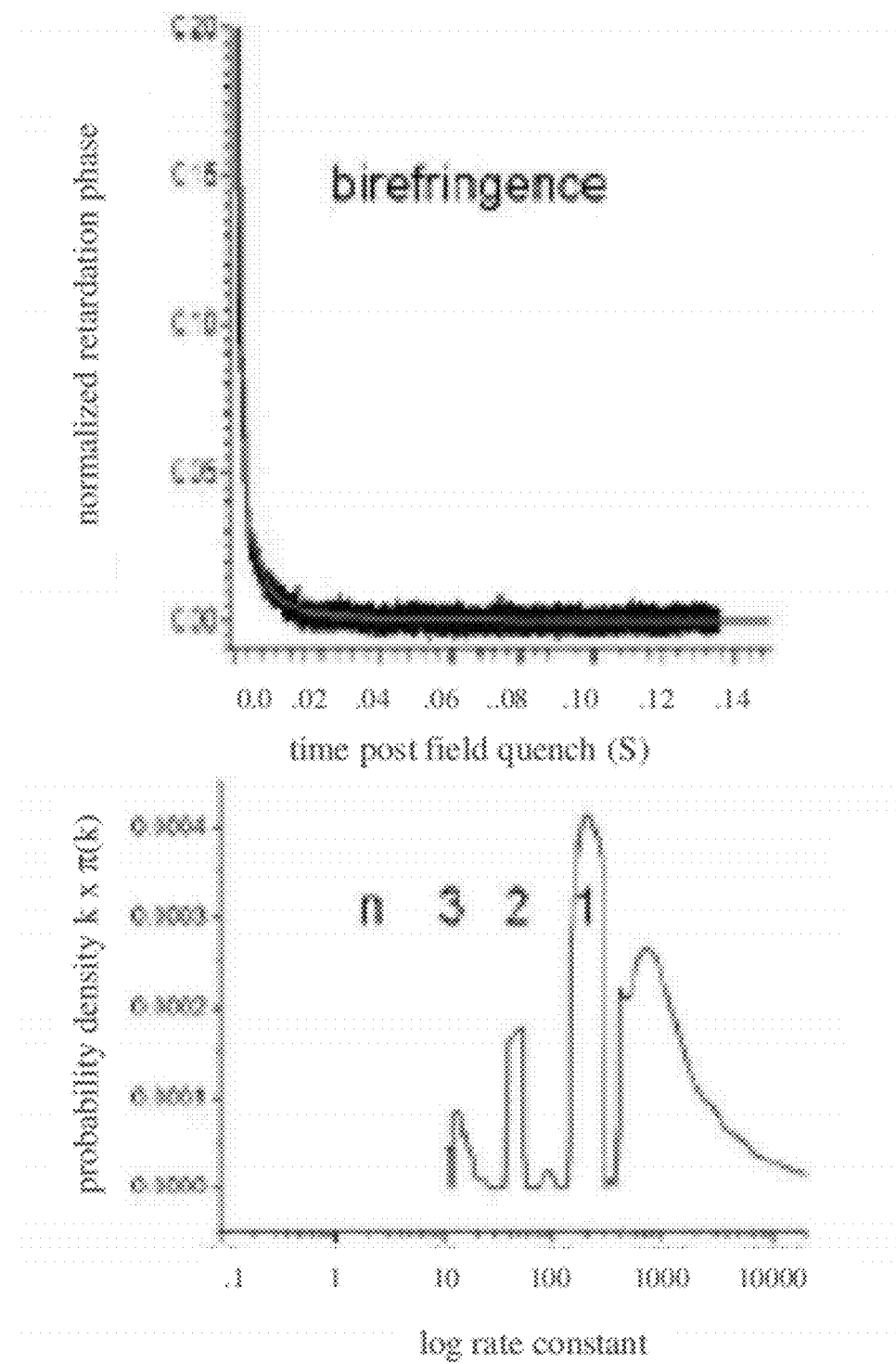
FIG. 5A presents a birefringence relaxation curve and the associated distribution of rotational rate constants determined from the relaxation curve.
Figure 5B:
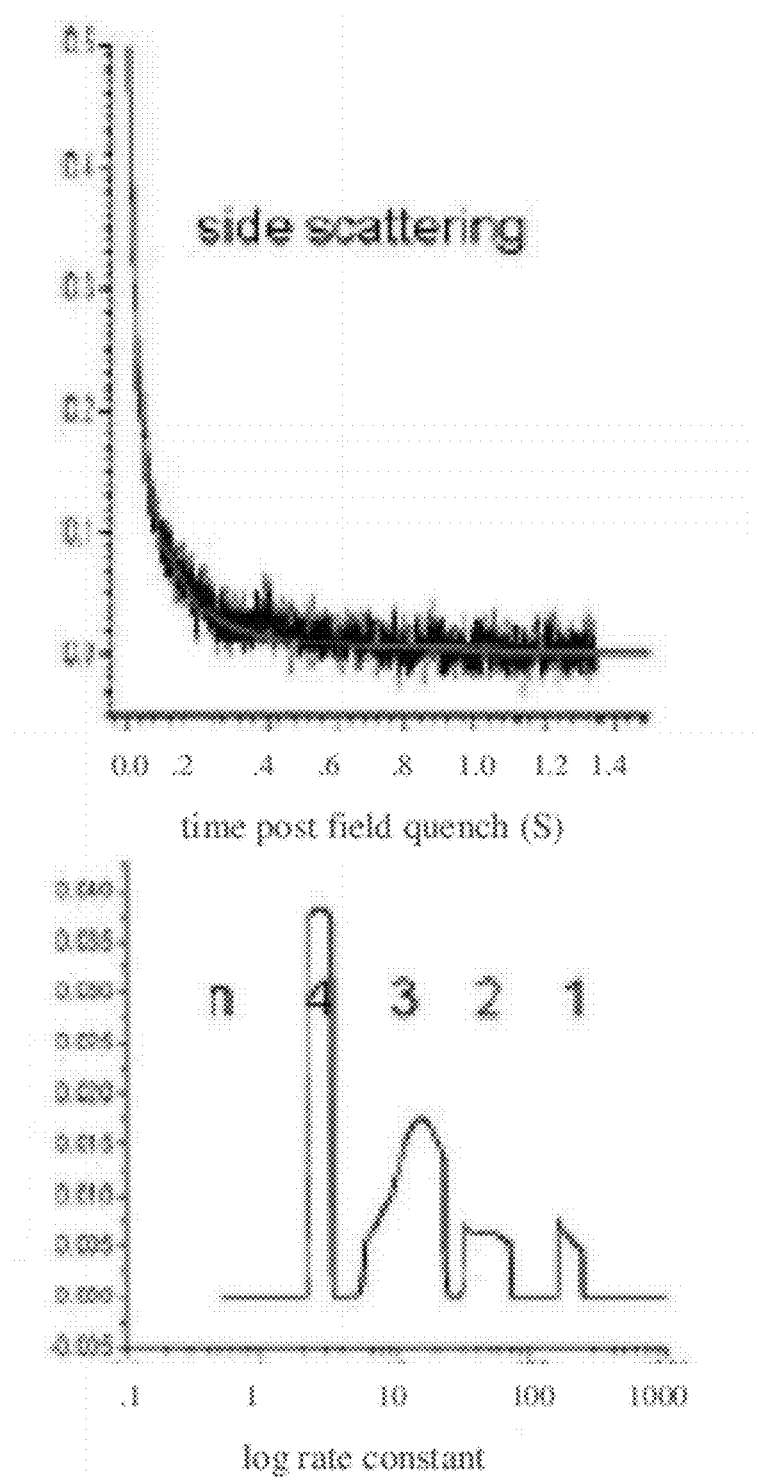
FIG. 5B presents a side scattering relaxation curve and the associated distribution of rotational rate constants determined from the relaxation curve.
Figure 5C:
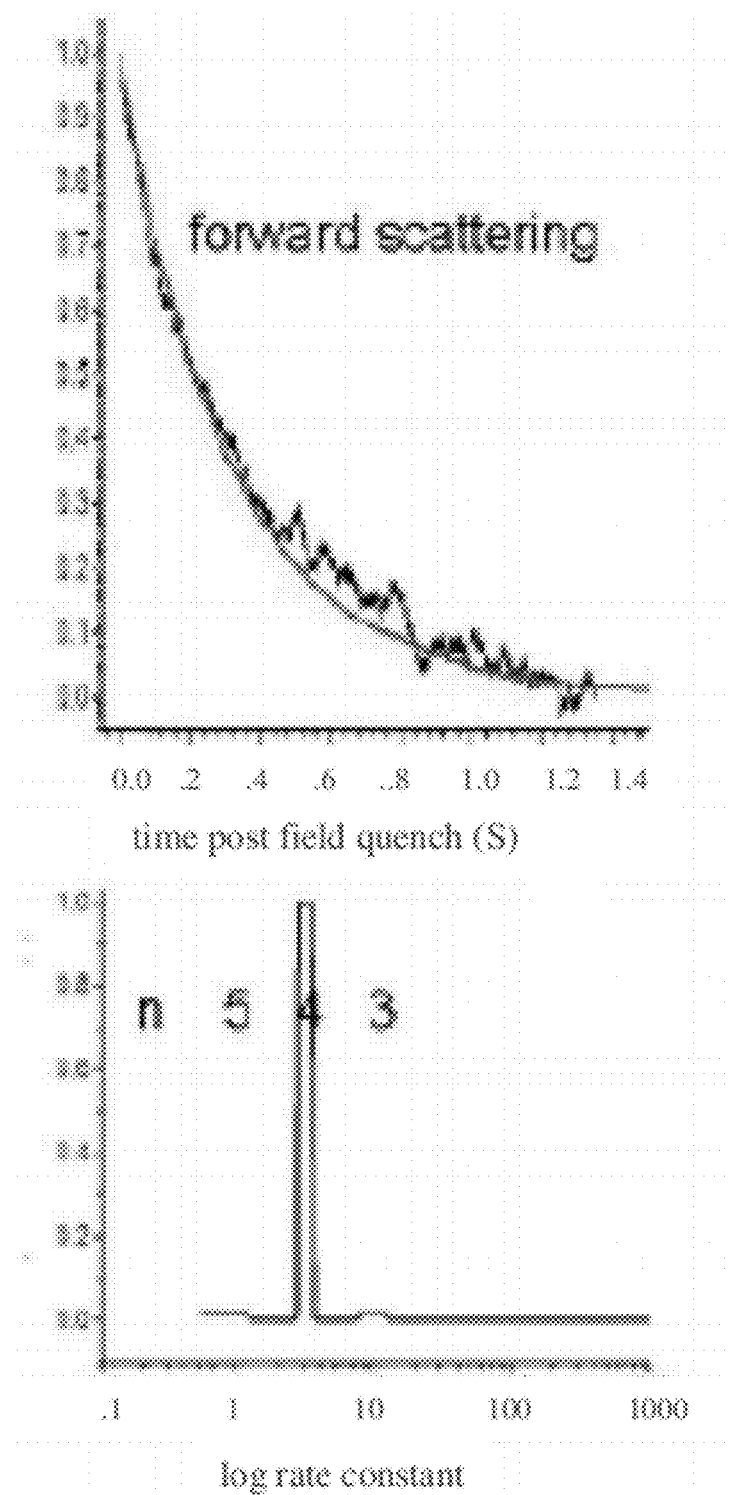
FIG. 5C presents a forward scattering relaxation curve and the associated distribution of rotational rate constants determined from the relaxation curve.

As an example of this spectral analysis the relaxation spectra from FIG. 5 was used to evaluate the respective rate constants and probability distributions for virus-nanoparticle complex rotation. FIG. 5A shows the rate constant distribution obtained by inverse transformation of the normalized birefringent phase delay, while FIG. 5B shows the rate constant distribution obtained from normalized side scattering and FIG. 5C shows the rate constant distribution obtained from normalized forward scattering. Only the birefringence phase delay signal shows any contribution from uncomplexed magnetic particles. This contribution is characterized by a spectrum of rotational rate constants faster than 230 sec$^{-1}$. Below this cutoff rate, the virus complexes begin to appear. Their rates appear to fall into discreet bands that we designate as rotational modes (n=1,2,3, etc). The probability density functions for each of these modes was calculated by the phase function reconstruction method of Zhou and Zhuang and appear in FIGS. 5A, B, and C. These probabilities were used, together with the rate constants they represent to reconstruct the original relaxation curves (shown in FIGS. 5A, B, and C). It is clear that side and forward scattering detects some of the same modes as birefringence phase delay. However, the weight (probability density) associated with the slower rotating modes is greater for scattering detection, than for birefringence phase detection. The discreet rotational modes are associated with different numbers of virus particles comprising the clusters.

Figure 6:
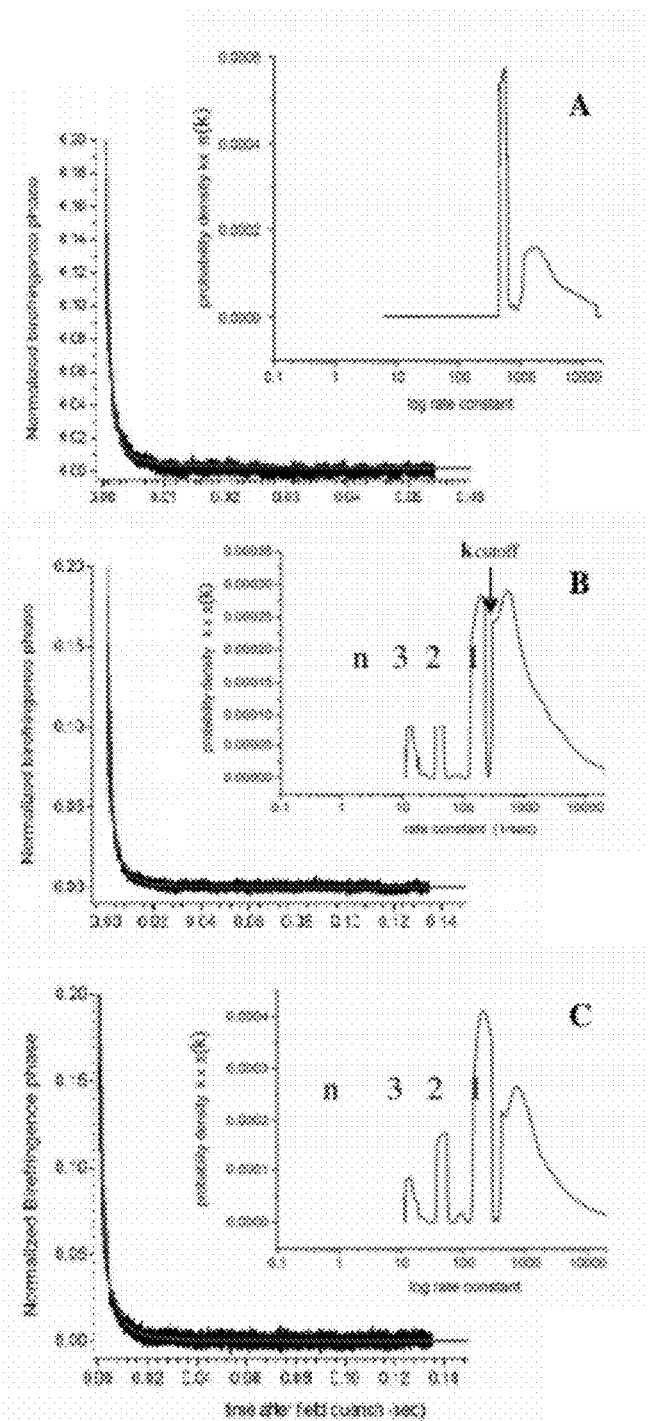
FIG. 6A presents a birefringence relaxation curve for a virus titer of 0 pfu/mL and the associated distribution of rotational rate constants determined from the relaxation curve.
FIG. 6B presents a birefringence relaxation curve for a virus titer of 1,100 pfu/mL and the associated distribution of rotational rate constants determined from the relaxation curve.
FIG. 6C presents a birefringence relaxation curve for a virus titer of 5,500 pfu/mL and the associated distribution of rotational rate constants determined from the relaxation curve.
Figure 7:
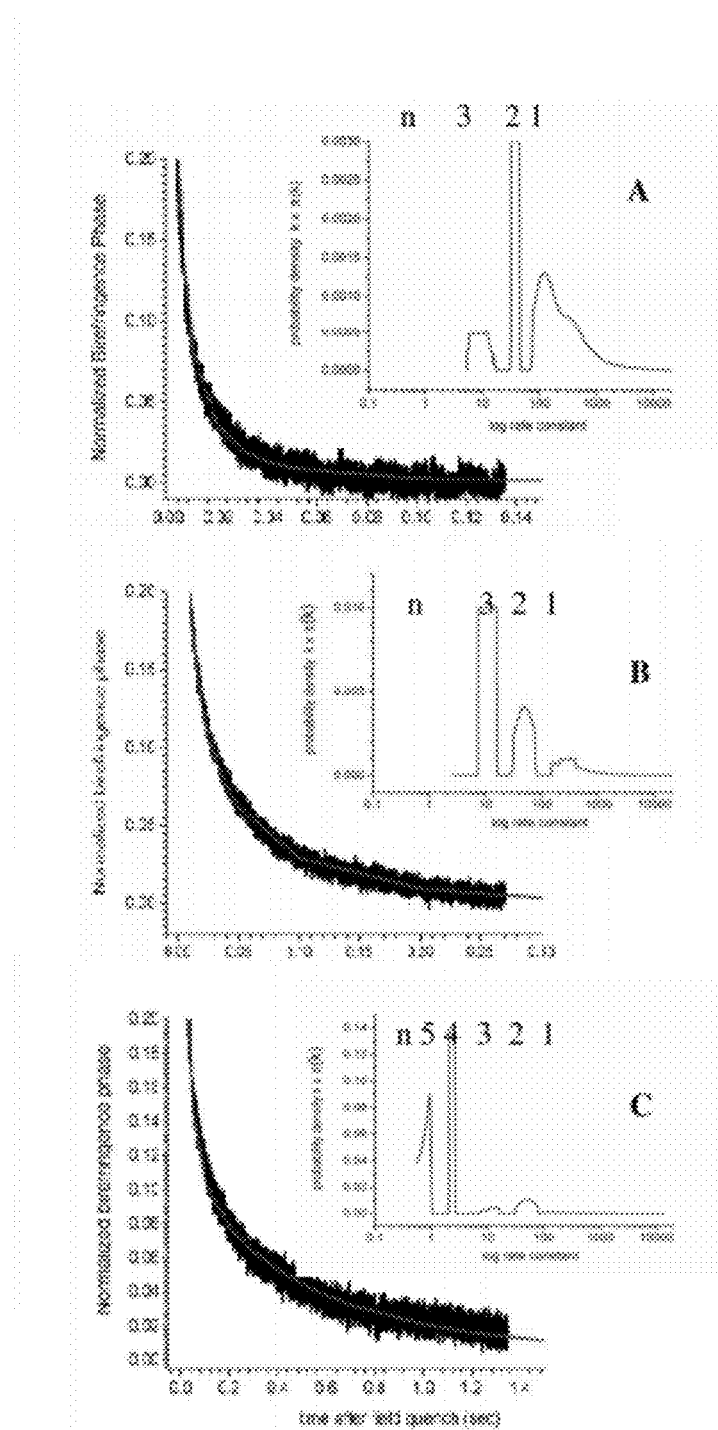
FIG. 7A presents a birefringence relaxation curve for a virus titer of 80,000 pfu/mL and the associated distribution of rotational rate constants determined from the relaxation curve.
FIG. 7B presents a birefringence relaxation curve for a virus titer of 120,000 pfu/mL and the associated distribution of rotational rate constants determined from the relaxation curve.
FIG. 7C presents a birefringence relaxation curve for a virus titer of 300,000 pfu/mL and the associated distribution of rotational rate constants determined from the relaxation curve.

FIGS. 6 and 7 show the relaxation dynamics and the modal distributions obtained from birefringence data on increasing virus titers to a fixed concentration of nanoparticles. FIG. 6A presents the results for a titer of 0 pfu/mL VSV, i.e. the phase delay due to 10$^{10}$ Streptavidin decorated maghemite nanoparticles with 3 μg of biotinylated I1 mAb attached by biotin linkage. FIG. 6B presents the normalized phase delay from a parallel sample of magnetic nanoparticles to which a titer of 1,100 pfu/mL VSV was added. FIG. 6C presents the phase delay dynamics on addition of a titer of 5,500 pfu/mL VSV. Similarly, FIG. 7 shows that normalized phase delay under conditions of greater viral burden. FIG. 7A presents the results for a titer of 80,000 pfu/mL. FIG. 7B presents the results for a titer of 120,000 pfu/mL. FIG. 7C presents the results for a titer of 300,000 pfu/mL. In each case, the rate distributions were evaluated and used to reconstruct the original relaxation dynamics. Experiments shown in FIGS. 6 and 7 demonstrate: a) the existence of a cutoff rotational frequency, below which all particles are bound to virus, and above which all particles are free; b) as more virus is titrated into a constant amount of nanoparticles multiple rotational modes emerge, which may be called n(k). The function n(k) physically represents the nanoparticle bridging of n virus particles into multiple virus particle complexes. In each case, experimental traces are overlaid by the birefringence phase reconstructions generated from the depicted rate constant distributions.

$$\text{Load} = N \int_0^{k_{cutoff}} n(k)\pi(k)kdk \quad (2)$$

Here π(k) is the reconstructed probability density that a rotational rate between k and k+dk is present in the mixture. It is weighted by the rotational mode number, n(k), that describes the number of virion particles per cluster. The integral is evaluated up to a cutoff rate k<kcutoff; which is the minimum rotational rates of free nanoparticles. The normalization constant N accounts for the variation of birefringence phase shift with total nanoparticleconcentration ($N_T$), and the average number of nanoparticles binding to the monomer target.

Figure 8:
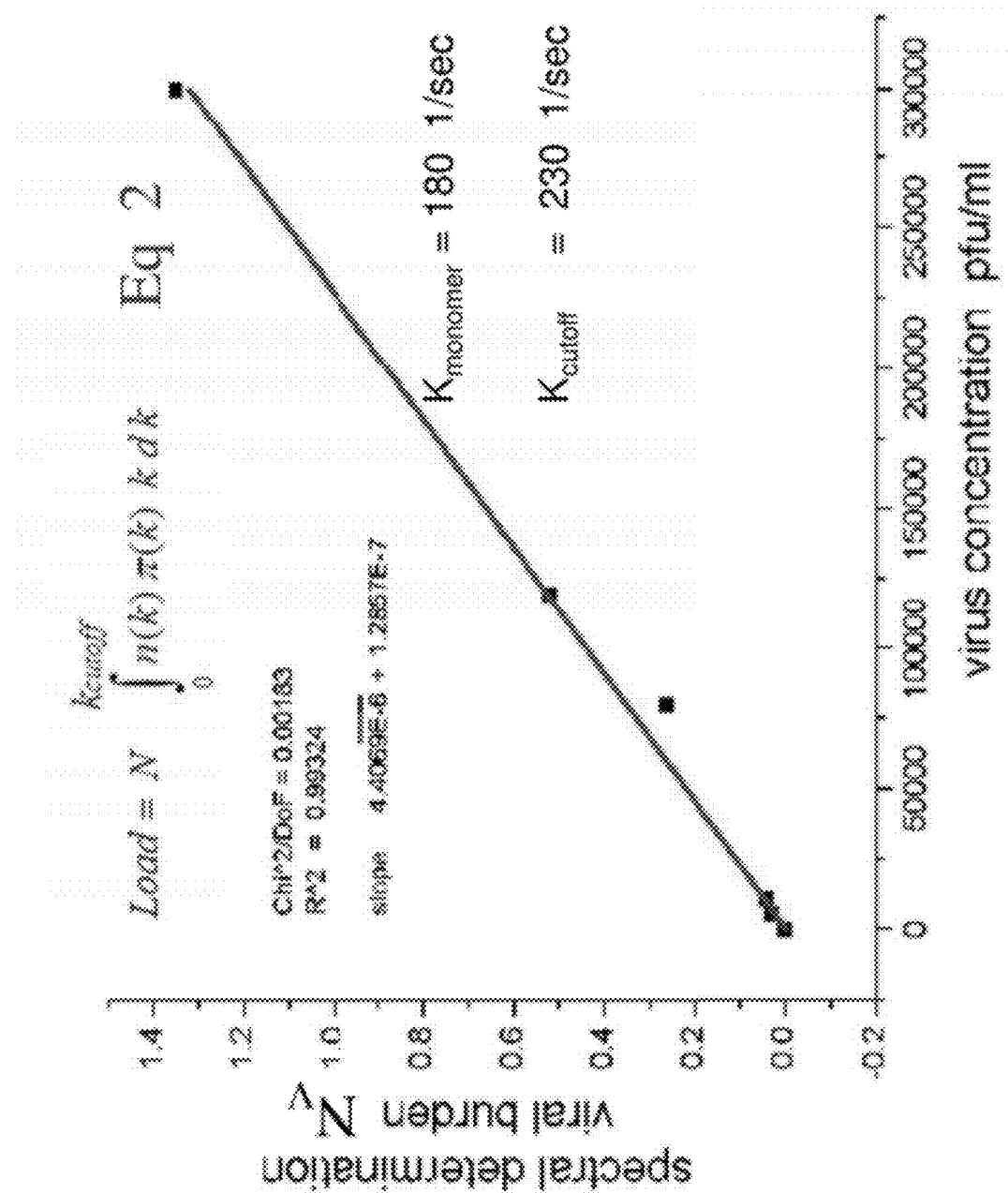
FIG. 8 is a graph of the calculated viral load determined from the cumulative probability of forming complexes exhibiting rotational rates below a cutoff rate weighted by the number of virus particles contained within the complexes versus the titer of added virus.
Figure 9:
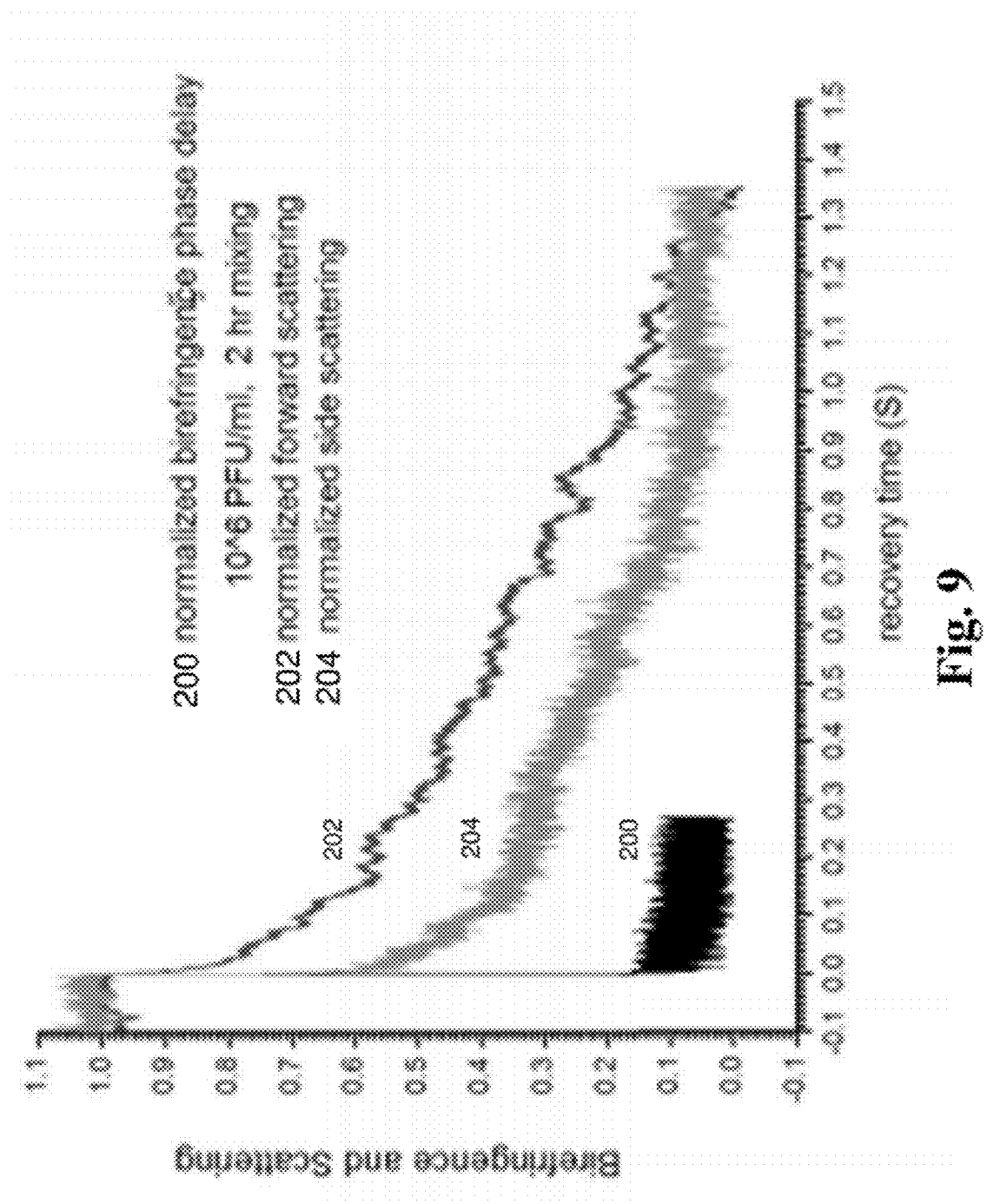
FIG. 9 is a graph of signal intensity versus recovery time for birefringence, forward scattering, and side scattering.

Viral load, in general, can be evaluated from the cumulative probability distributions of rate constants representing the bound vs. free nanoparticle fractions. From this modal picture of cluster development, an expression can be formulated to determine viral load in the sample using eq. 2. This model assumes the modal number reflects the number of virus particles bound together in a complex. It further assumes the existence of an average number of nanoparticles binding to each virus particle. It is known that there are between 400-1000 epitopes on the VSV envelope to which I1 mAb will bind. In eq 2, N is equal to the ratio between the total number of nanoparticles in the sample ($10^{10}$) and the average number binding to each virus particle. The integral in eq. 2 is evaluated up to a cutoff rate k<kcutoff; which is the minimum rotational rates of free nanoparticles. FIG. 8 plots the cumulative probability of virus/nanoparticle aggregates weighted by the number of virus particles each carries vs the titer of added virus. The regression gives a linear dependence with high correlation ($R^2$=0.993) and low variance (Chi square=0.0018). The conclusion is that viral load can be quantified from such inverted spectral transformations using a linear regression to relate the cutoff integral to the number of virions present. From the experimental slope of FIG. 8, N was found to be equal $4.4 \times 10^{-6}$. Because the number of virus copies present for an RNA virus is typically found to be between ~100 times the number of infectious copies present, we calculate the average number of binding nanoparticles per virus particle to be 440.

Figure 10:
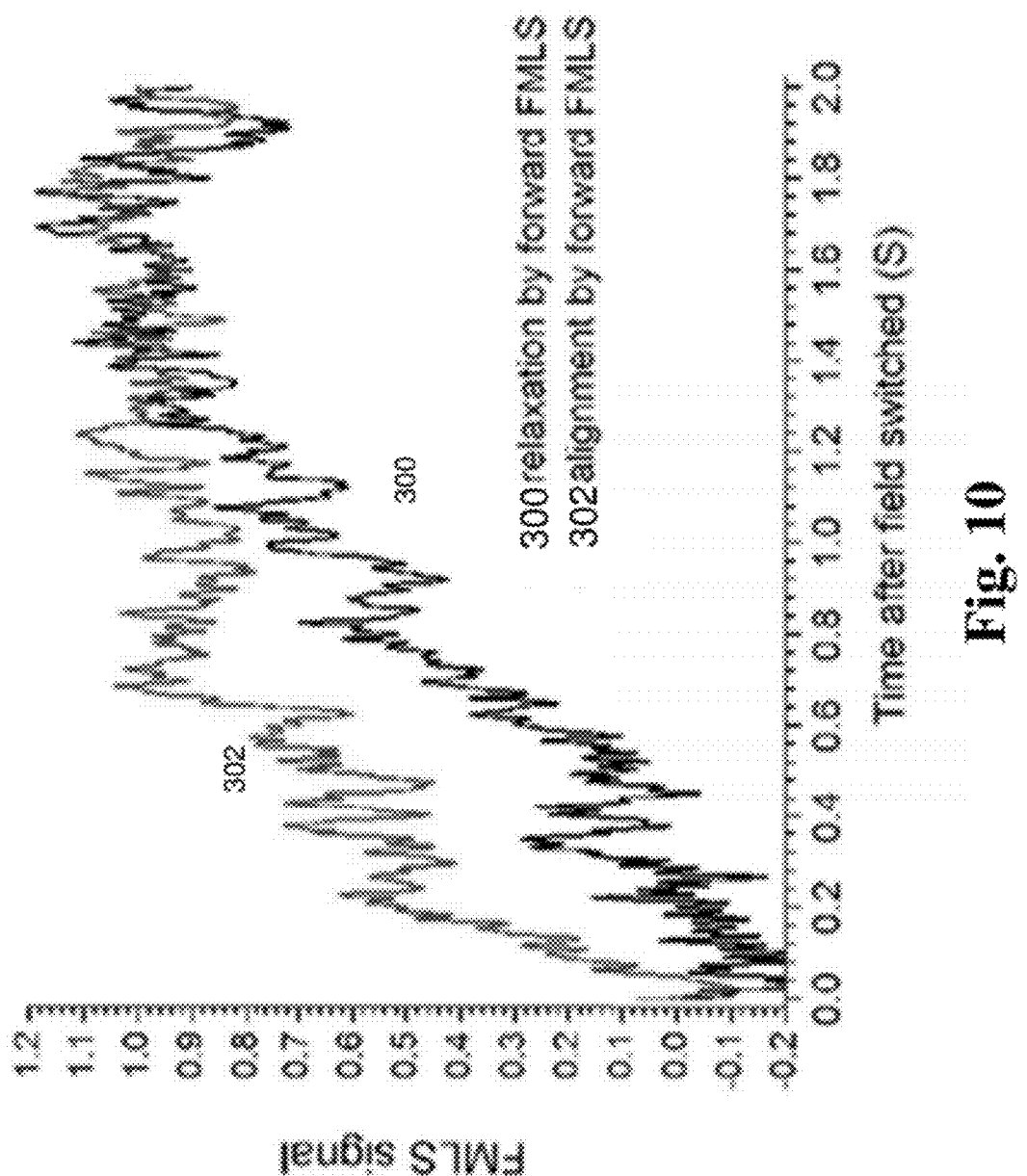
FIG. 10 is a graph of forward light scattering intensity versus time for alignment (Step On) and relaxation (Step Off) phases of particle rotation.

The virus load was augmented in an experiment incubating $10^{10}$ Staphylococcal protein G/I1 mAb conjugates with $10^6$ pfu/ml VSV. The field modulated birefringence 200, side 204 and forward 202 light scatter relaxation signals are shown in FIG. 9. Interestingly, the birefringence signal 200 amplitude dropped to less than 20% of the signal amplitude under 0 viral load. This was significantly greater than the losses that could be accounted for by light scatter. The light scatter relaxation dynamics suggest that many virus-nanoparticle complexes were formed, resulting in a high density of nanoparticles on the surface of the viral envelope. The proximity of these nanoparticles may have caused their magnetic moments to interact with each other as well as the orienting field. This could have caused the particles to magnetically attract closer together and merge into larger magnetic clusters that lose their birefringence properties. They still retain their magnetism, however, that can be used to orient virus with the applied field. The birefringence signal 200 in FIG. 9 exhibits two main components: one fast relaxing component presumably due to free nanoparticles, and a slow relaxing component, presumably due to virus bound nanoparticles.

The side scatter signal 204 in FIG. 9 exhibits at least three distinct components: the fastest band presumably due to single virus complexes (>20 Hz), a second centering at ~12 Hz may be attributed to double virion complexes, and a third band centering at ~1.5 Hz, is due to three or more virion particles held together by nanoparticle bridges linking multiple virus particles together. The forward scattering 202 in FIG. 9 also shows the presence of higher multimers of virus. The relaxation time course of the forward scatter signal has extended to beyond 1.5 sec.

Example 3

Relaxation from Light Scattering of Magnetically Oriented Membrane Vesicles

It was demonstrated that optical monitoring of field modulated relaxation dynamics can be applied to discovery of cloned recombinant proteins, with specific reference to a cloned β adrenergic receptor protein. Presumed advantages of this screening modality are "label free" detection, no requirement for extensive target purification, quantitative, high speed sample analysis preformed either in static wells, or under flow conditions, direct from a bioreactor.

Targeting Human $\beta_2$ Adrenergic Receptor Cloned in Spheroplasts

Alprenolol is a synthetic non-selective beta blocker that ligand binds with high affinity for human $\beta_2$ adrenergic receptor. The following set of experiments utilized the ability of the receptor protein to bind to alprenolol as a means to detect recombinant β adrenergic protein in bacterial expression systems. Bacterial spheroplasts were generated from *E. coli* cultures that were cloned to express receptor protein. Ligand-receptor bioassays were performed by monitoring the association of spheroplasts with alprenolol derivatized nanoparticles.

Alprenolol Derivatization of Meito Sangyo Maghemite Nanobeads.

In a typical reaction, alprenolol HCl (50 mg, $1.77\times10^{-4}$ mol) and 6-amino-1-hexanethiol, and HCl (25 mg, $1.47\times10^{-4}$ mol) were added to a small round-bottomed flask and dissolved in water (200 μl). The reaction mixture was extensively purged with $N_2$ and kept under a $N_2$ atmosphere to avoid alprenolol oxidation and disulfide formation. The mixture was heated to 90° C. and potassium persulfate (4.0 mg, $1.47\times10^{-5}$ mol) dissolved in water (200 μl) was added in 20 μl aliquots over two hours. The progress of the reaction was followed by TLC (89% acetone, 10% methanol, 1% ammonium hydroxide). Addition of 1M NaOH (200 μl) resulted in formation of a precipitate. This material was extracted into chloroform (300 μl). The product was then extracted back into the aqueous layer with 300 μl of 0.67 M HCl. This solution was degassed with $N_2$ and stored in a tightly-sealed tube at −20° C. An aliquot was diluted in methanol to approximately 0.1 mg/ml and submitted to the FAS Mass Spectrometry Resource (Harvard University) for ESI (Electrospray) analysis.

Carboxy-dextran coated maghemite nanoparticles were obtained from Meito Sangyo Co (~$1\times10^{14}$ particles/ml, ~200 COOH groups/particle). Buffer exchange with 25 mM MES (pH=5) was performed on a 100 μl aliquot using an Amicon Ultracel 30,000 MWCO centrifugal filter device (Millipore Inc.) with a final volume of 500 μl. EDC (0.4 mg, $2.1\times10^{-6}$ mol) and sulfo-NHS (1.1 mg, $5.1\times10^{-6}$ mol) were added and the reaction was allowed to proceed at room temperature for 30 minutes. The activated nanobead solution was split into three portions, each with approximately $1.1\times10^{-9}$ mol. COOH surface groups. The alprenolol ligand modified with 6-amino-1-hexanethiol was diluted into 0.1 M sodium bicarbonate buffer (pH=8.3) and 0, 0.1, or 10 equivalents were added to each portion of nanoparticles. The reaction was allowed to proceed at room temperature for two hours and then quenched with 10 mM hydroxylamine. Unreacted small molecules were removed on a PD-10 desalting column (GE Healthcare, Inc.) equilibrated with PBS. The degree of alprenolol substitution was estimated to be 10%.

Spheroplast Preparation.

Spheroplasts were prepared by enzymatic digestion of the bacterial cell wall according to Witholt et al. An efficient procedure for the formation of spheroplasts from variously grown *Escherichia coli*. This procedure is widely accepted and is based on the combination of lysozyme treatment and osmotic shock followed by stabilization of the cell membrane by addition of $Mg_2$+ ions in the concentration range of 2-20 mM. Cell densities were based on previous determinations (with outer membrane present) and are expressed as milligrams of cell dry mass per milliliter. 40 mg/ml dry weight was routinely used in the preparative process, and finally, after adding the membrane stabilizer and performing several washes, the spheroplasts were resuspended in volumes that were identical with the starting 40 mg/ml of cell dry mass concentration.

Birefringence phase delay and field modulated light scattering measurements typically employed a 700 μl reaction volume in which we equilibrated ligand-derivatized nanobeads with spheroplasts. HEPES buffer, fortified with protease inhibitors was combined with 50 μl nanobeads (approximate density is: 1-2×10¹⁰ particles/ml) with variable amounts of spheroplasts (from 5 to 50 µl). The reaction mixture was incubated at 4° C. with gentle rocking for 2 hours. These mixtures were used, without separation of the reactants directly for optical measurements (FIG. 10). Field modulated light scattering measurements (FMLS) were obtained in the presence and absence of *E. coli* spheroplasts expressing recombinant G protein coupled receptors at varying times after mixing. FIG. 10 shows the forward scatter FMLS signals obtained after 15 minutes of mixing under relaxation (300) and orientation (302) phases of magnetization. The conjugates in the absence of spheroplasts exhibited sub-millisecond rate time constants. In the presence of bacteria expressing these proteins, forward field modulated light scattering 300 detected in the step-off phase exhibited an average relaxation rate constant of ~0.9 s⁻¹, corresponding to a spheroplast diameter of 1400 nm, FIG. 10. This was larger than the average spheroplast size of 1000 nm determined by birefringence relaxation measurements. The time course to spheroplast orientation was followed by forward field modulated light scattering 302 and it was found that maximal alignment was achieved ~0.7 s after turning on a magnetic pulse. The field had a flux density of 80 gauss.

Example 4

Field Dependent Light Scattering from Magnetically Oriented Bacteria

Another example of the use of field modulated light scattering is the detection and identification of bacteria that might be used as a weapon of bioterrorism. *Francisella tularensis* is a non-motile bacterium of cylindrical shape, 200 nm across and 200 nm long ($V_h$=6.3×10⁶ nm³). It is the causative agent of tularemia, with variable symptoms that localize as ulcerative glandular, oculo-glandular, oro-pharyngeal and pneumonic lesions. It can be acquired either through an animal bite, by skin contact, or through respiratory inhalation or ingestion.

Maghemite nanoparticle conjugates were synthesized by combining Miltenyi Staphlococcal protein G µMACS reagent with a mouse monoclonal antibody directed to the cell wall lipopolysaccharide of *Francisella* strain Schu-S4. The nanoparticles were incubated for two hours with the bacteria to allow sufficient time for binding.

Figure 11:
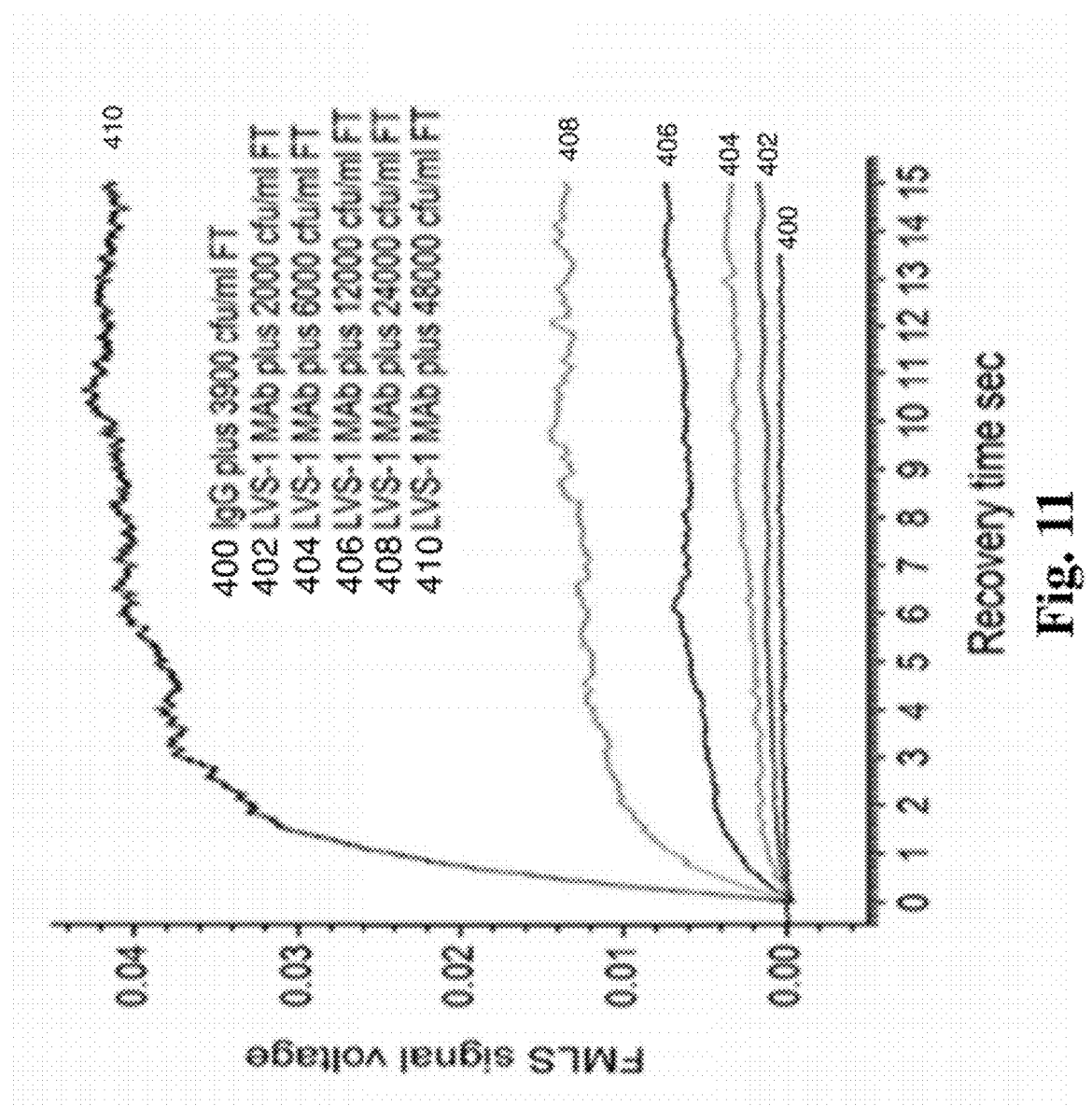
FIG. 11 is a graph of forward scatter signals versus recovery time after field quenching for different concentrations of *Francisella tularensis* (Ft) bacteria and a fixed density of particles.

Scattered light was intercepted at θ=15° by a photomultiplier detector. The sample was illuminated with 632 nm polarized light. The illuminated volume was 20 µl. FIG. 11 shows the forward scatter signals from suspensions containing various particle densities of *Francisella tularensis* bacteria and a fixed density of maghemite nanoparticles (10¹⁰ particles/ml). The particle densities were 3,900 cfu/ml for curve 400, 2,000 cfu/ml for curve 406, 24,000 cfu/ml for curve 408, and 48,000 cfu/ml for curve 410. Curves 402-410 were obtained using the bacterium-specific LVS-1 mAb, while curve 400 was obtained using an irrelevant IgG antibody coupled to the nanoparticles. The data were acquired after the application of a 100 gauss orienting pulse lasting for four seconds (20% duty cycle). The repetition rate was 50 mHz. The data represent the averages of ten repeated acquisitions. In these plots, the voltage signal increases corresponding to a decreasing light intensity after the orienting magnetic pulse is switched off. The apparent time constant for the rise of scatter from negative control (irrelevant antibody) was consistent with a small component of coherent scatter due to antibody conjugates present in the original preparation that had aggregated before bacteria addition. These were generated, presumably, because of the possibility for multiple attachment sites for IgG type antibodies on protein G beads, enabling the coupling of multiple beads through the same antibody molecule.

Figure 12:
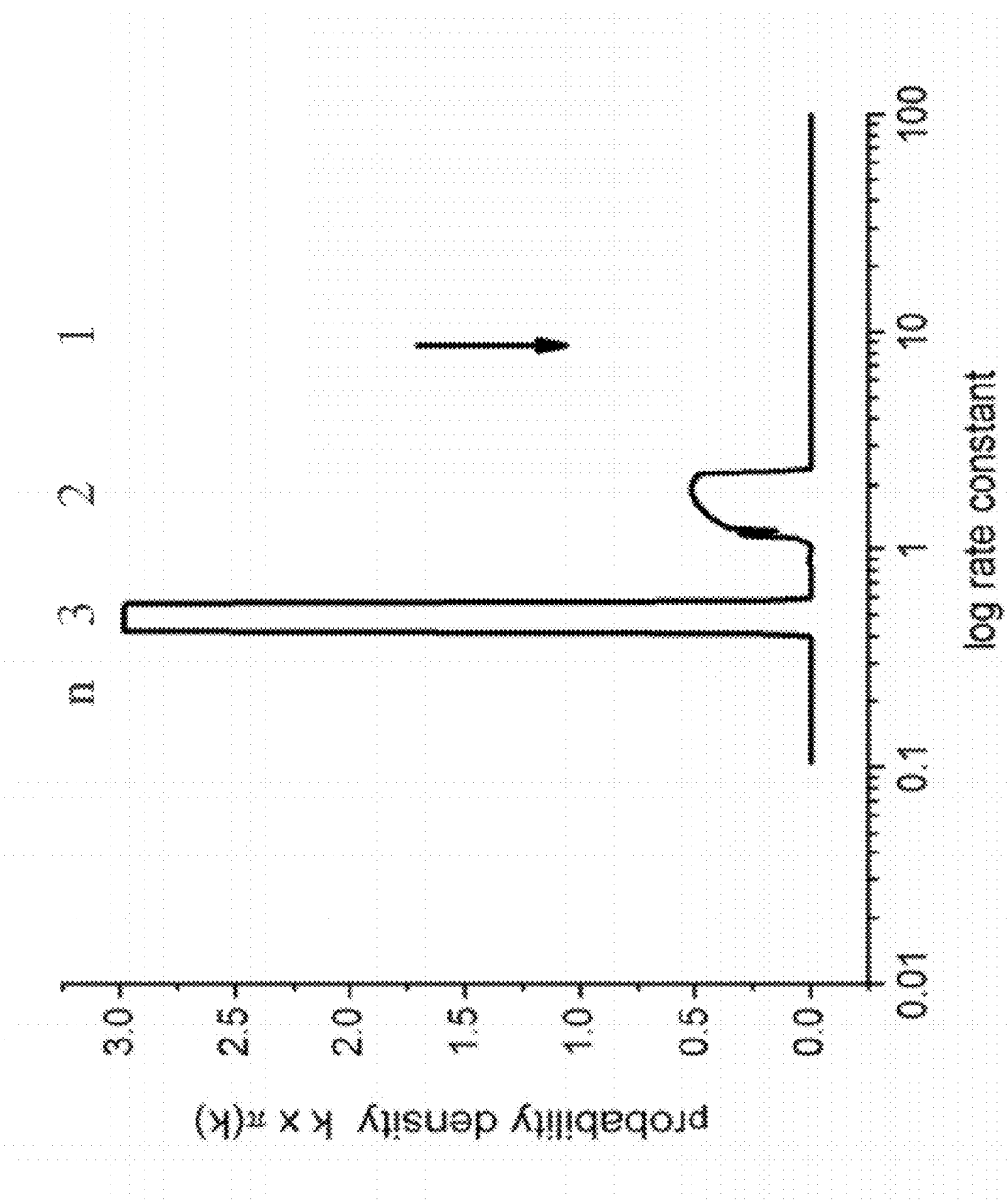
FIG. 12 is a graph of the rotational rate constant distribution of a sample of Ft bacteria at high burden based on relaxation of forward scattering.
Figure 13:
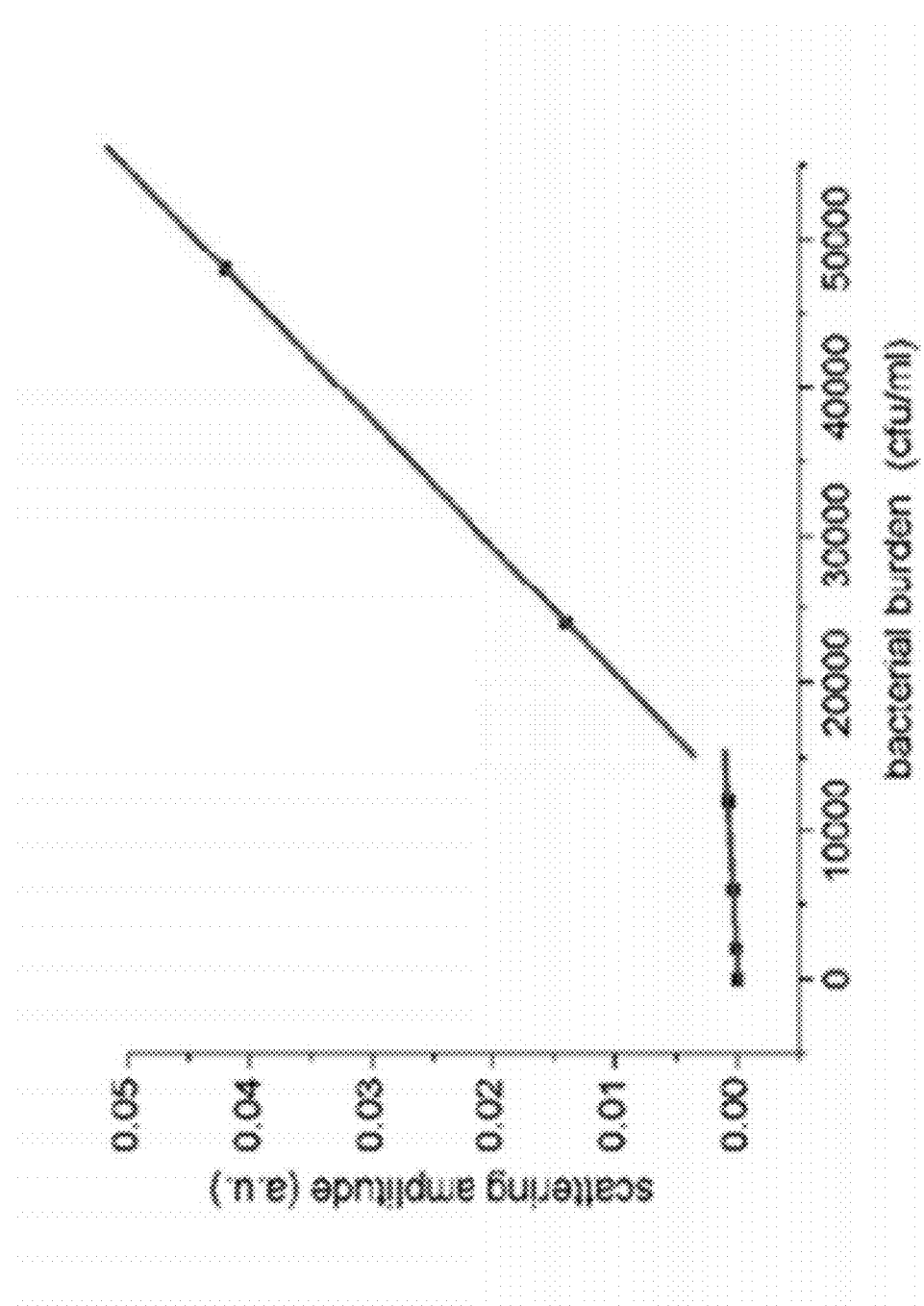
FIG. 13 is a graph of the maximum scattering amplitudes versus bacterial burden indicating bacteria aggregate into multimeric complexes at higher bacteria burdens.

Enhanced scattering intensity occurred on the replacing the irrelevant nanoparticle conjugates with relevant a *Francisella* nanoparticle conjugates. The minimum *Francisella* detected coherently by forward scatter with field modulation was 1300 cfu/ml or ~26 cfu in the interrogated volume. Based on the accepted size of this bacterium, Brownian theory suggests *Francisella* should exhibit a rotational relaxation time of about 7 milliseconds in physiological saline. The minimum relaxation time obtained from forward scatter signals at low load was 20 msec, suggesting that the minimal scattering unit detected two bacteria complexes. The signals showing a relaxation of 3-4 seconds (FIG. 12) at high bacterial concentrations infers that the major scattering complex intercepted by forward light scattering has a diameter of several microns. Rate constants extracted from intermediate bacterial additions exhibited rate constants of 2 and 0.4 s⁻¹, representing aggregates containing 5 and more bacteria. The maximum scattering amplitude obtained from this series of measurements was plotted against the amount of added bacteria to see if such a plot could be used to obtain a calibration for bacterial load (FIG. 13). It was found that the plot produced a curvilinear relationship due to the formation of increasingly large bacterial aggregates at growing bacteria burden.

Example 5

Field Modulated Light Scattering and Birefringence Phase Delay for Sequence Specific Detection of Product Generation of Isothermal Nucleic Acid Amplification Reactions in Real Time An inactivated HIV-1 clade B subtype LIA was obtained, with certified copy information from Zeptometrix Corp. of Buffalo, N.Y. 2,000 iu. was aliquoted and processed these using Qiagen's Viral RNA Isolation kit into thirteen 15 µl volume fractions (150 i.u./fraction or ~10 i.u./µl) each. Estimated recovery of gene product was based on 100% collection efficiency. Curtis et al. identified six LAMP amplification primers for a p24 gene template [ref]. They were synthesized by Integrated DNA Technologies of Coralville, Iowa and were used here as the panel of LAMP primers.

Figure 14:
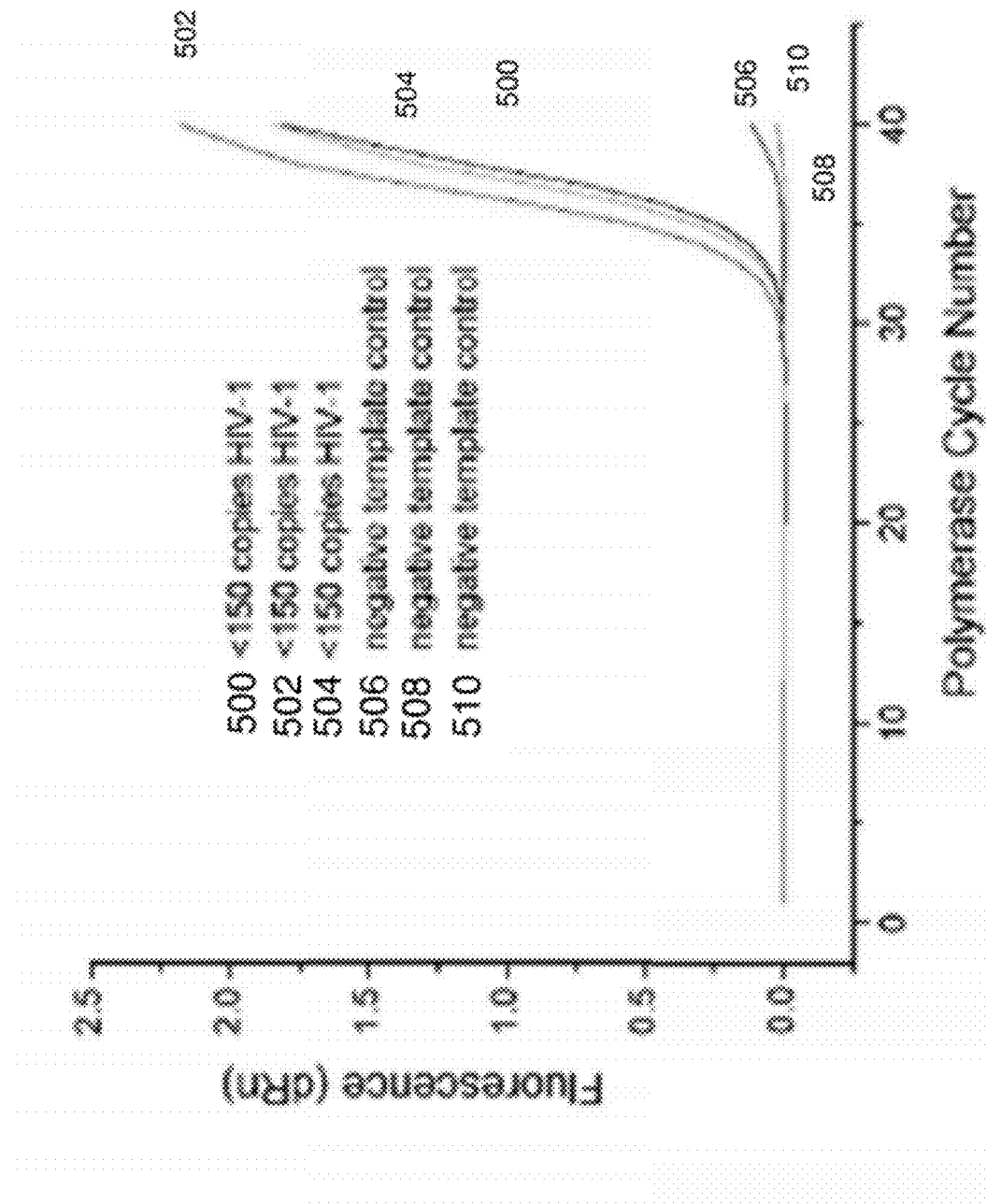
FIG. 14 is a graph depicting the time course of product generation from HIV-1 template RNA by reverse transcription polymerase chain reaction (RT-PCR)

To confirm actual harvest of viral RNA in the isolation step qRT-PCR was performed. Reverse transcription was applied to the 15 µl fractions of digest using the Backward LAMP B3 outer primer at 42° C. and M-MuLV reverse transcriptase. The reaction was stopped after 60 minutes by raising the temperature to 80° C. Five microliters of the cDNA product mixture, corresponding to less than 20 HIV genomes, was then aliquoted into each of three PCR tubes. A hotstart version of *Thermus brockianus* DNA polymerase was added according to the manufacturer's directions (Finnzymes Inc. and New England Biolabs Inc.) along with the forward and reverse LAMP primers, F3 and B3 (0.1 µM each). Water samples were used as zero template controls curves 506, 508, and 510 in FIG. 14. SybrGreen fluorescence was monitored for up to 40 cycles. FIG. 14 shows the time course of product development starting with <20 copies of HIV-1 RNA curves 500, 502, and 504. The average threshold cycle ($C_T$) was 35.41±0.71 for the HIV isolates; while it was >40 for the negative template control.

Figure 15A:
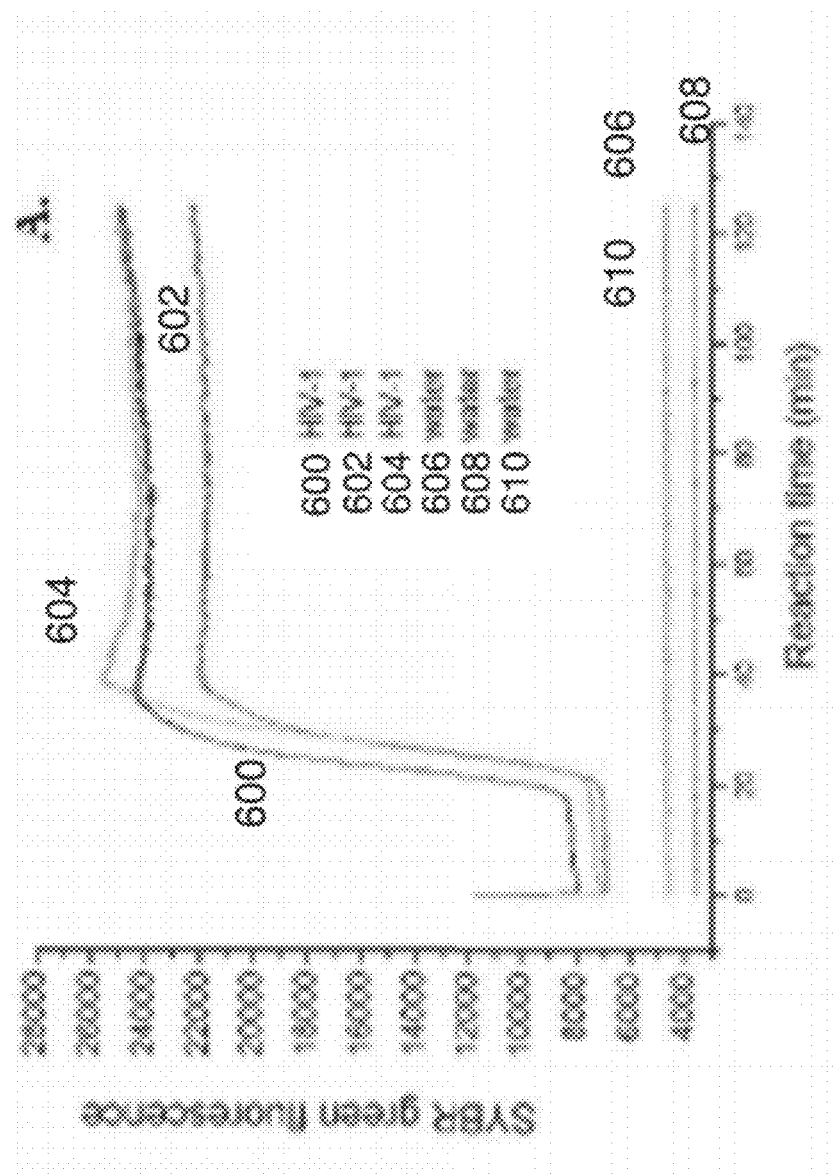
FIG. 15A is a graph depicting the time course of generating stem-loop DNA products by Loop Assisted Isothermal Amplification (LAMP) from ~150 template copies of HIV-1 RNA.

The LAMP bioassay was also run at 63° C. using the set of six primers recommended by Curtis et al. in a reagent mixture of 50 µl volume. SYBR green fluorescence was used as the indicator of double strand DNA product formation. These data were obtained on a Stratagene MX3005 PCR instrument. The rates of product generation using HIV-1, and no RNA templates present, were compared. Approximately 150 i.u of HIV-1 RNA was added in a triplicate set of tubes. In another triplet set, an equivalent volume of water provided the negative template control curves 606, 608, and 610 in FIG. 15A. FIG. 15A shows the time course of generating DNA LAMP stem-loop product from each template, curves 600, 602, and 604.

Figure 15B:
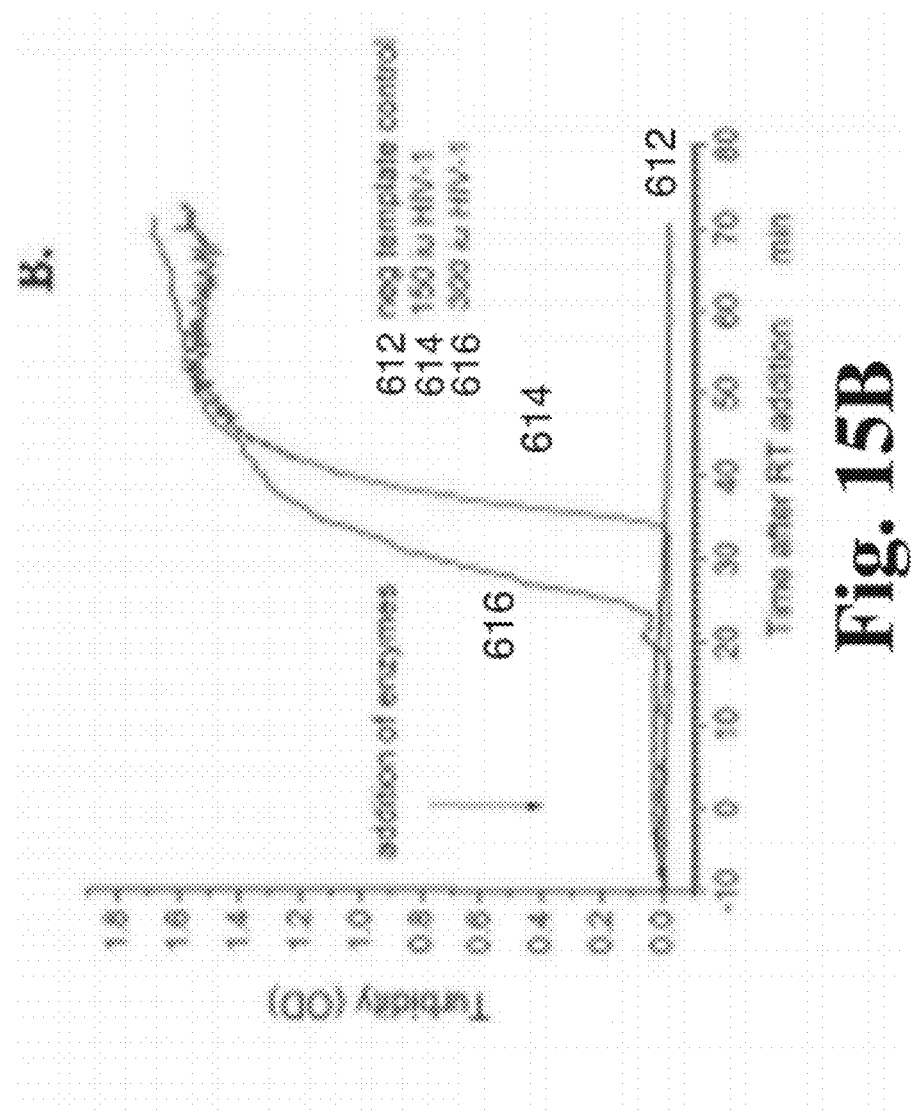
FIG. 15B is a graph depicting the turbidity resulting from $Mg_2PO_4$ generated during LAMP amplification of HIV-1 RNA.

The LAMP amplification bioassay was then performed in single 100 µl tubes, tracking the reaction in real time by measuring the increasing turbidity at 488 nm due to the generation of $Mg_3PO_4$ precipitate a by-product of the polymerization reaction. The reaction was monitored in a custom-built instrument in which the reactor was maintained in a constant temperature bath set at 63° C. FIG. 15B shows the turbidity rise for the same bolus of HIV-1 RNA (<150 copies) curve 614 that was used in the LAMP amplification bioassay of FIGS. 17A. As depicted in FIG. 15B, turbidity was measured as the log of the ratio of light transmitted through the sample with respect to a reference beam that bypassed the sample. Turbidity threshold time has been shown to be an indicator of the concentration of original virus template present. The results show that, indeed, real-time turbidity measurements, in combination with LAMP amplification protocols, have the capacity to detect low levels of virus. That measurable magnesium pyrophosphate is generated is an indication of high yield of DNA generated from the LAMP reaction. The turbidity bioassay was repeated with twice the viral sample curve 616 and again with a zero template control curve 612. The results infer that the time till onset of turbidity, just as the time till onset of fluorescence may be used to determine the initial viral load.

Figure 16A:
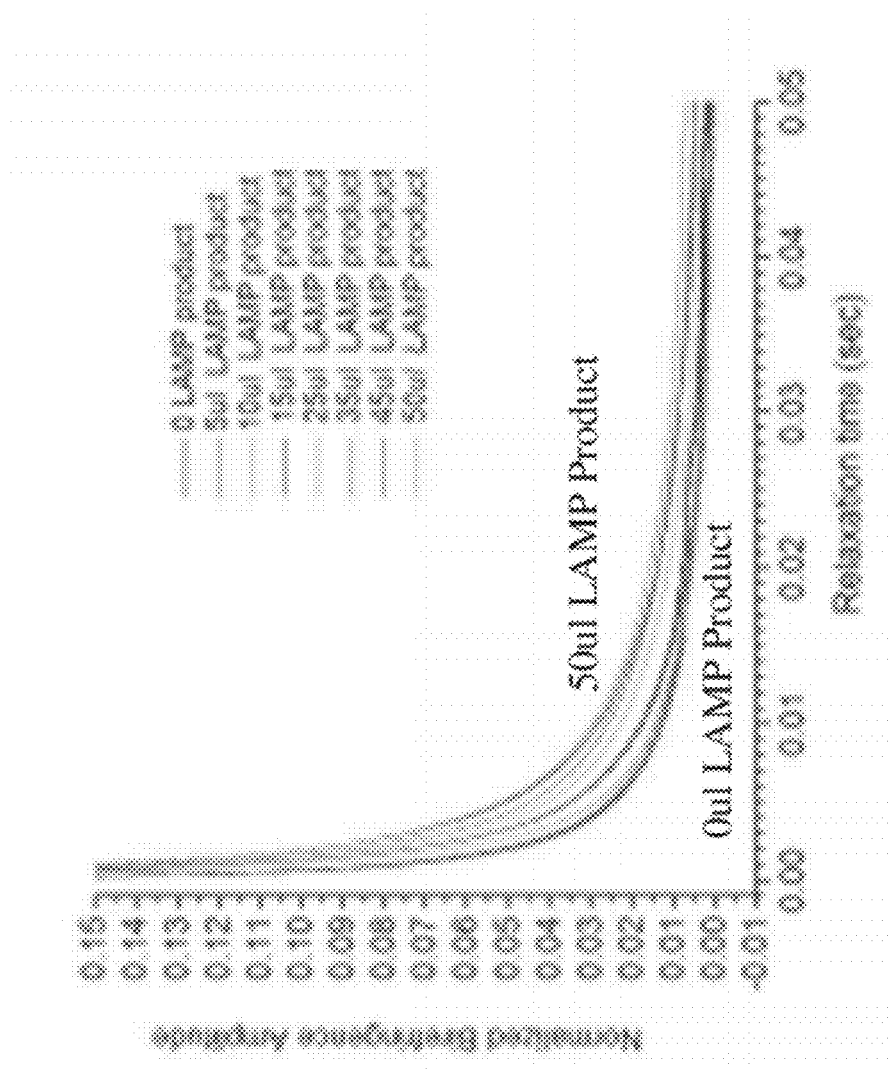
FIG. 16A is a graph of normalized birefringence retardation phase versus relaxation time for various volume additions of LAMP product to a fixed density of particles.
Figure 16B:
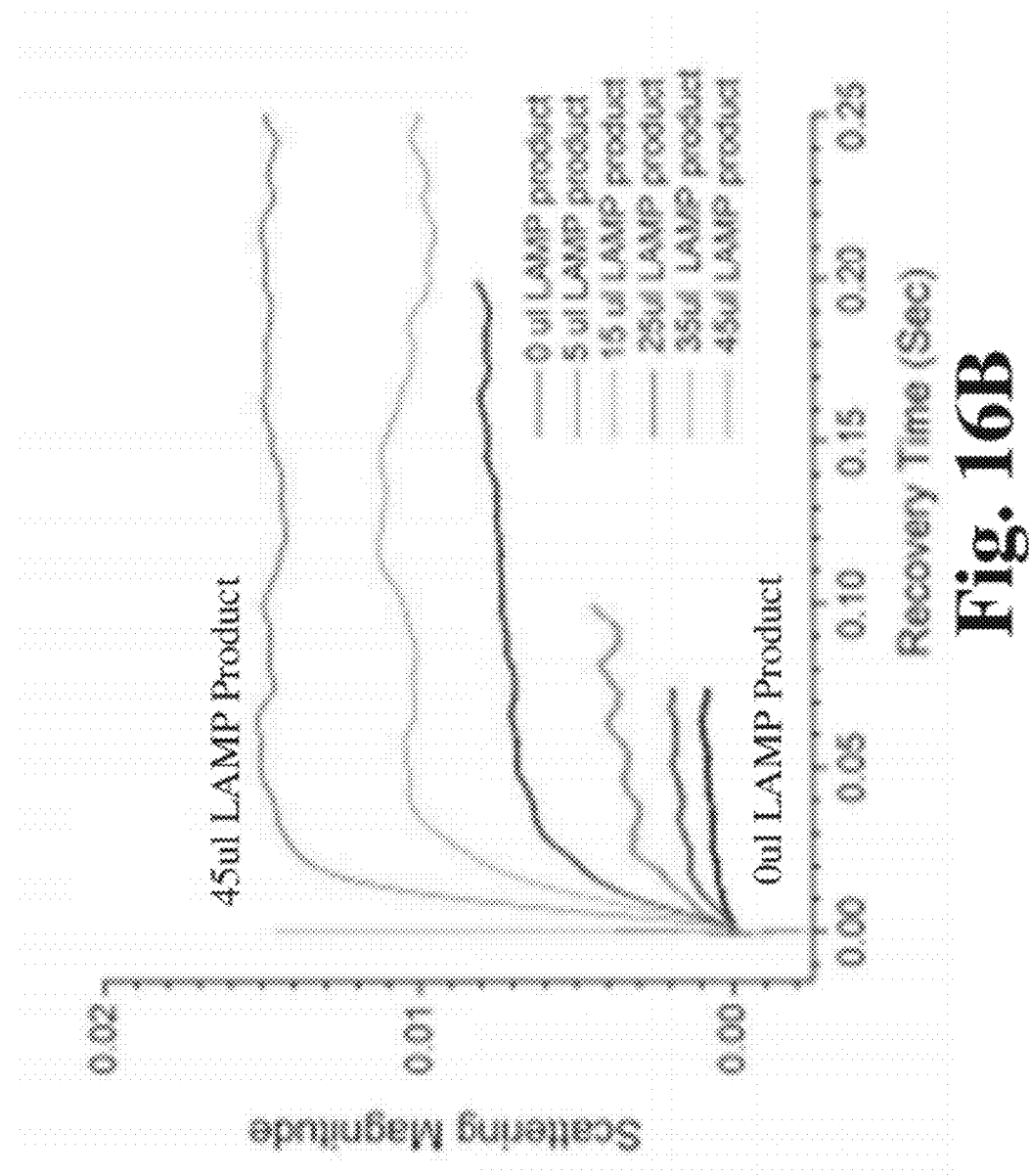
FIG. 16B is a graph of forward scattering intensity versus relaxation time for various volume additions of LAMP product to a fixed density of particles.

The turbidity and fluorescence probes, however, are not sequence-specific, and occasionally self priming or primer dimerization have been shown to be capable of promoting polymerization of primer-primer duplexes. For this reason, sequence-specific probes that are capable of real-time readout are preferred for more accurate quantitative analysis. To develop a sequence-specific probe, we synthesized Loop B primers having TEG-biotin at the 5' termination. Using these and the previous series of LAMP primers we prepared a new set of LAMP products, monitoring the time course of the reaction until turbidity measurements indicated a change of 2 OD units. The biotinylated Loop B primers are expected to integrate into the resulting stem-loop product structure, producing a high molecular weight double strand DNA cluster containing many biotin groups. The LAMP amplification was quenched by raising the reaction temperature to 80° C. and then titrated aliquots of the reaction mixture into a suspension of Strepavidin decorated maghemite nanoparticles (Miltenyi microMACS beads) at a concentration of approximately $10^{10}$ nanoparticles/ml. The results of this titration as monitored by birefringence relaxation (FIG. 16A) and by field modulated light scattering field modulated light scattering (FIG. 16B).

Figure 17:
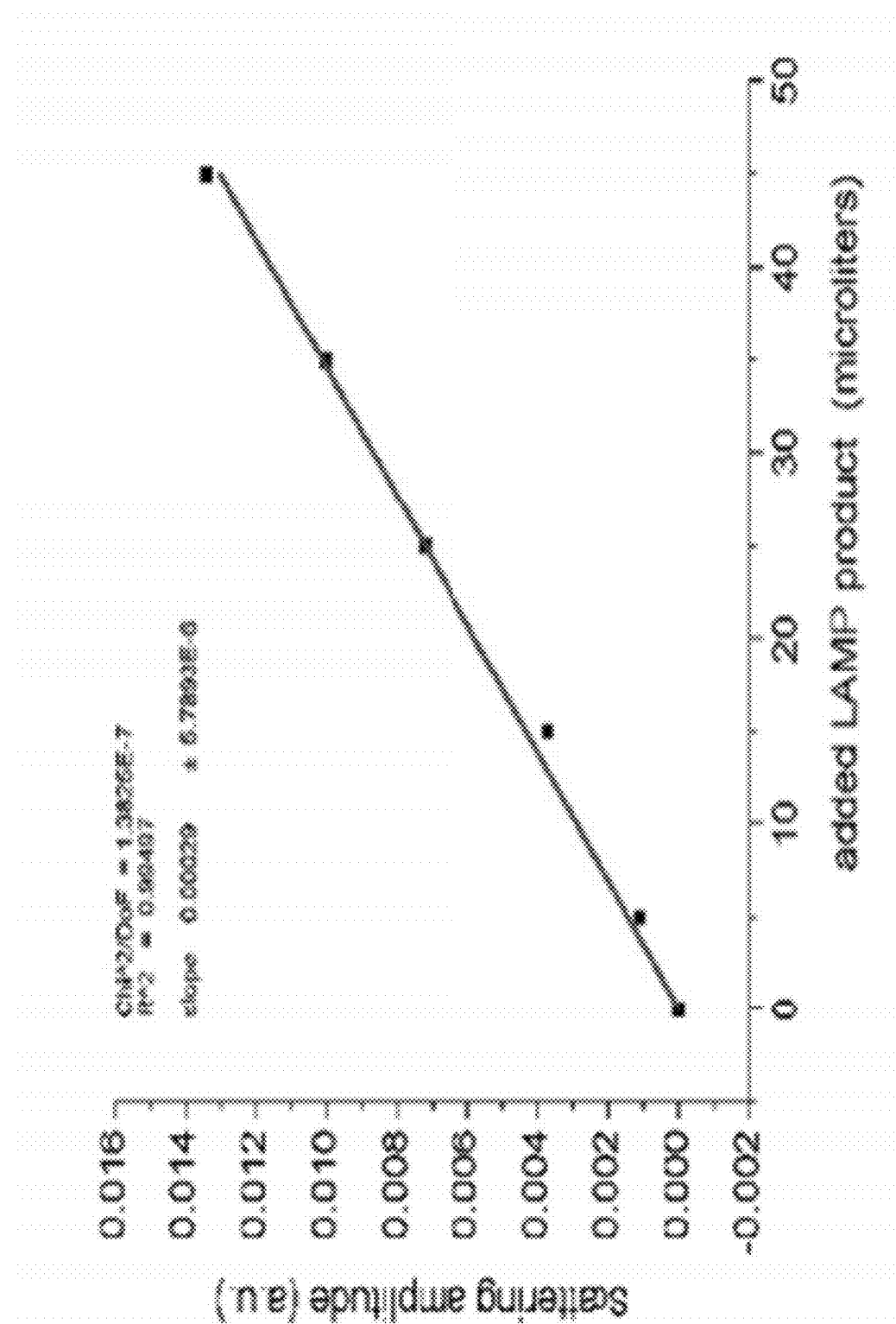
FIG. 17 is a graph of maximum forward scatter amplitude versus volume additions of LAMP product to a fixed density of particles.

The field modulated light scattering data were acquired at 15° forward scatter angle. Both birefringence relaxometry and field modulated light scattering indicate similar rotational relaxation time of the nanoparticle-LAMP product complexes (~10 msec) with increasing signal amplitude as more product is added and as shown in FIGS. 18A and 18B. It is apparent that field modulated light scattering yields the more easily interpretable signal amplitude that scales with product added. To prove this the measured difference in forward scattering amplitudes between the average plateau peak after LAMP product addition and the plateau peak before product addition was plotted as a function of added LAMP product (FIG. 17). As seen in FIG. 17, a linear regression resulted.

Example 6

Process to Evaluate and Reduce the Size Heterogeneity of Nanoparticle Conjugates.

Because of the sensitivity of light scattering to the presence of the largest agglomerates in a mixture, the technique of field modulated light scattering has been used to identify and quantify target/nanoparticle complexes in the above examples. In the following example it was used to evaluate and control the size of complexes to reduce their size heterogeneity that could result in target quantification errors, particularly if targets are comparable in size to the largest heterogeneity.

FIGS. 20A-20C compare the birefringence and field modulated light scattering signals from 50 nm aminated maghemite nanoparticles (obtained from Chemicell, Berlin, Del.) that were reacted with succimidyl iodoacetate to produce an iodated surface that could be reacted with thiolated oligonucleotides. 20 mer and 49 mer oligonucleotides were obtained as disulfide terminated hybridization probes (IDT Technologies, Coralville, Iowa), reduced, and reacted with the iodated maghemite nanoparticles. The measured relaxation spectra for each measurement method were analyzed to determine a relaxation constant which was then used to determine an approximate corresponding particle diameter from the graph presented in FIG. 2. The birefringence relaxation spectra show that the 20 mer decorated nanoparticles, curve 700, predominately exhibit a diameter less than 100 nm, while the 49 mer decorated particles, curve 702, exhibit an average diameter of 160 nm. The forward and side field modulated light scattering data, on the other hand indicate components 300 nm and higher as determined from curves 704, 706, 708 and 710. These minor oversized components could be removed by size exclusion chromatography and field modulated light scattering used to monitor their removal.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A method for analyzing a sample comprising:
   providing a sample that includes unbound magnetic particles and complexes that comprise one or more magnetic particles bound to a target;
   applying a first magnetic field to the sample for a first duration in a first direction;
   removing the first magnetic field from the sample;
   applying a second magnetic field to the sample for a second duration in a second direction substantially perpendicular to the first direction;
   removing the second magnetic field from the sample;
   directing light at the sample; and
   detecting at least one of birefringent phase delay in light emanating from the sample and anisotropic light scattered from the sample.

2. The method of claim 1, wherein the first magnetic field is perpendicular to a direction of light directed to the sample.

3. The method of claim 1, wherein the first duration is greater than the second duration.

4. The method of claim 1, wherein the first duration is selected to align substantially all of the complexes substantially parallel to the first direction.

5. The method of claim 1, wherein the second duration is selected to align substantially all of the unbound magnetic particles substantially parallel to the second direction.

6. The method of claim 5, wherein the second duration is less than a relaxation time associated with the complexes.

7. The method of claim 1, wherein the magnetic particles are magnetic nanoparticles.

8. A bioassay device comprising:
a sample area configured to include a sample that includes complexes that comprise one or more magnetic particles bound to a target;
a first magnetic field source constructed and arranged to apply a magnetic field in a first direction to the sample area;
a second magnetic field source constructed and arranged to apply a second magnetic field in a second direction to the sample area;
a light source constructed and arranged to direct light to the sample area; and
a detector assembly constructed and arranged to measure at least one of birefringent phase delay in light emanating from the sample and anisotropic light scattering from the sample.

9. A method for analyzing a sample comprising:
providing a sample that includes unbound magnetic particles and complexes that comprise one or more magnetic particles bound to a target;
applying a magnetic field to the sample;
removing the magnetic field from the sample;
detecting at least one of birefringent phase delay in light that is backwardly reflected from the sample and back-scattered light.

10. The method of claim 9 wherein the step of providing the sample further comprises providing the sample including primers, substrates and enzymes required for isothermal nucleic acid amplification that are capable of replicating a portion of template nucleic acids.

11. The method of claim 10 further comprising providing one or more hybridization probes chemically coupled to the bound and unbound magnetic particles.

12. The method of claim 9 further comprising providing one or more target ligands chemically coupled to the bound and unbound magnetic particles.

13. The method of claim 12 wherein providing the sample further comprises providing the sample including cell or cell fragments, possessing protein expression systems or systems that express membrane embedded, recombinant proteins.

* * * * *